US007205104B2

(12) United States Patent
Remacle et al.

(10) Patent No.: US 7,205,104 B2
(45) Date of Patent: Apr. 17, 2007

(54) IDENTIFICATION OF BIOLOGICAL (MICRO) ORGANISMS BY DETECTION OF THEIR HOMOLOGOUS NUCLEOTIDE SEQUENCES ON ARRAYS

(75) Inventors: José Remacle, Malonne (BE); Sandrine Hamels, Loverval (BE); Nathalie Zammatteo, Jambes (BE); Laurence Lockman, Bastogne (BE); Sophie Dufour, Mons (BE); Isabelle Alexandre, Leave (BE); Francoise De Longueville, Jambes (BE)

(73) Assignee: Eppendorf Array Technologies SA (EAT), Namur (BE)

( * ) Notice: Subject to any disclaimer, the term of this patent is extended or adjusted under 35 U.S.C. 154(b) by 0 days.

(21) Appl. No.: 09/817,014

(22) Filed: Mar. 23, 2001

(65) Prior Publication Data

US 2002/0106646 A1 Aug. 8, 2002

(30) Foreign Application Priority Data

Mar. 24, 2000 (EP) ................................. 00870055
Sep. 15, 2000 (EP) ................................. 00870204

(51) Int. Cl.
*C12Q 1/68* (2006.01)
*C12P 19/34* (2006.01)

(52) U.S. Cl. ...................... 435/6; 435/91.1; 435/91.2
(58) Field of Classification Search .................. 435/6, 435/91.1, 91.2, 4; 536/23.1, 23.5, 23.6, 23.7, 536/24.3, 24.33, 25.32

See application file for complete search history.

(56) References Cited

U.S. PATENT DOCUMENTS

| | | | |
|---|---|---|---|
| 5,143,854 A | 9/1992 | Pirrung et al. ............... 436/518 |
| 5,312,527 A | 5/1994 | Mikkelsen et al. ....... 205/777.5 |
| 5,445,934 A | 8/1995 | Fodor et al. ..................... 435/6 |
| 5,451,512 A * | 9/1995 | Apple et al. ............... 435/91.2 |
| 5,510,270 A | 4/1996 | Fodor et al. ................. 436/518 |
| 5,552,270 A | 9/1996 | Khrapko et al. ............... 435/6 |
| 5,587,307 A | 12/1996 | Alborn, Jr. et al. |
| 5,683,872 A | 11/1997 | Rudert et al. ................... 435/6 |
| 5,723,591 A | 3/1998 | Livak et al. |
| 5,736,257 A | 4/1998 | Conrad et al. ........... 428/474.4 |
| 5,770,721 A | 6/1998 | Ershov et al. |
| 5,800,992 A * | 9/1998 | Fodor et al. ..................... 435/6 |
| 5,807,522 A * | 9/1998 | Brown et al. .................. 422/50 |
| 5,821,060 A | 10/1998 | Arlinghaus et al. ............ 435/6 |
| 6,207,648 B1 | 3/2001 | Waxman et al. |
| 6,228,575 B1 | 5/2001 | Gingeras et al. |
| 6,255,059 B1 * | 7/2001 | Klein et al. ................. 435/7.31 |
| 6,306,643 B1 * | 10/2001 | Gentalen et al. ......... 435/287.2 |
| 6,331,441 B1 | 12/2001 | Balch et al. |
| 6,488,932 B1 * | 12/2002 | Boon et al. ............... 424/185.1 |
| 6,541,617 B1 * | 4/2003 | Bamdad et al. ............ 536/23.1 |
| 2002/0102578 A1 | 8/2002 | Dickinson et al. |
| 2003/0198943 A1 | 10/2003 | Remacle |
| 2005/0106126 A1 | 5/2005 | Whitlock |
| 2006/0003308 A1 | 1/2006 | Kullisch |

FOREIGN PATENT DOCUMENTS

| | | |
|---|---|---|
| EP | 0511559 | 11/1992 |
| EP | 0476014 | 8/1994 |
| EP | 0535242 | 9/1997 |
| GB | 2318791 | 6/1998 |
| WO | WO 89/11548 | 11/1989 |
| WO | WO 94/05695 | * 3/1994 |
| WO | WO 95/11995 | 5/1995 |
| WO | WO 97/10364 | 3/1997 |
| WO | WO 97/27317 | 7/1997 |
| WO | WO 97/27329 | 7/1997 |
| WO | WO 97/29212 | 8/1997 |
| WO | WO 98/11253 | 3/1998 |
| WO | WO 98/28444 | 7/1998 |
| WO | WO 99/16780 | 4/1999 |
| WO | WO 99/35499 | 7/1999 |
| WO | WO 00/72018 | 11/2000 |

OTHER PUBLICATIONS

Shchepinov et al. (Nuc. Acid Res. (1997) 25(6): 1155-1161).*
Anthoney et al. Rapid diagnosis of bacteremia by universal amplification of 23S ribosomal DNA followed by hybridization to an oligonulcleotide array. Journal of Clinical Microbiology vol. 38:781-788.*
Shchepinov et al. 1997. Nucleic Acid Research vol. 25:1155-1161.*
Guschin et al. Oligonucleotide microchips as genosensors for determinative and environmental studies in microbiology. Appl Environ Microbiol. Jun. 1997;63(6):2397-402.*
Martineau et al. Correlation between the resistance genotype determined by multiplex PCR assays and the antibiotic susceptibility patterns of *Staphylococcus aureus* and *Staphylococcus epidermidis*. Antimicrob Agents Chemother. Feb. 2000;44(2):231-8.*

(Continued)

*Primary Examiner*—Kenneth R. Horlick
*Assistant Examiner*—Heather G. Calamita
(74) *Attorney, Agent, or Firm*—Knobbe, Martens, Olson & Bear, LLP

(57) ABSTRACT

A method for identifying or quantifying an organism by a detecting its nucleotide sequence among at least 4 other homologous sequences comprising amplifying nucleic acids from the organism to generate target nucleotide sequences to be detected; contacting the target nucleotide sequences with single stranded capture nucleotide sequences bound by a single predetermined link to an insoluble solid support and discriminating the binding of a target nucleotide sequence specific of an organism with a signal resulting from a hybridization by complementary base pairing between the target nucleotide sequence and its corresponding capture nucleotide sequence is disclosed. The capture nucleotide sequence is bound to the insoluble solid support at a specific location on an array having a density of at least 4 different bound single stranded capture nucleotide sequences/cm$^2$. The location of the signal on the array allows identification or quantification of the organism.

22 Claims, 4 Drawing Sheets

OTHER PUBLICATIONS

Van Ness et al. A versatile solid support system for oligodeoxynucleotide probe-based hybridization assays *Nucleic Acids Research*, 19 3345-3350. 1991.

Guo, et al., Direct fluorescence analysis of genetic polymorphisms by hybridization with oligonucleotide arrays on glass supports, *Nucleic Acids Research*, 22:5465, 1994.

Anthony, et al., Rapid diagnosis of bacteremia by universal amplification of 23S ribosomal DNA followed by hybridization to an oligonucleotide array *Journal of Clinical Microbiology*, 38:781-788.

Wetmur, et al., Kinetics of renaturation of DNA *J. Mol. Biol.*, 31:319-370, 1968.

Fodor, et al., Multiplexed biochemical assays with biological chips. *Nature*, 364:555-556, 1993.

Apostolidis, et al., "Genetic differentiation and phylogenetic relationships among Greek Salmo trutta L. (brown trout) populations as revealed by RFLP analysis of PCR amplified mitochondrial DNA segments," Heredity, (1996) 77(6): 608-618, abstract only.

Musser, "Antimicrobial Agent Resistance in Mycobacteria: Molecular Genetic Insights," Clinical Microbiol Rev, (1995) 8(4):496-514.

Rose, et al., "Consensus-degenerate hybrid oligonucleotide primers for amplification of distantly related sequences," Nuc. Acid Res. (1998) 26(7): 1628-1635.

Maskos, U. et al. (1992) "Oligonucleotide hybridizations on glass supports: a novel linker for oligonucleotide synthesis and hybridization properties of oligonucleotides synthesized in situ" Nucleic Acids Research 20:1679-1684.

Schena, M., et al. (1996) "Parallel human genome analysis: microarray-based expression monitoring of 1000 genes" PNAS USA 93:10614-10619.

Wu, D.Y. et al. (1989) "The ligation amplification reaction (LAR)—amplification of specific DNA sequences using sequential rounds of template-dependent ligation" Genomic 4:560-569.

Zammatteo et al. (1997) "Comparison between microwell and bead supports for the detection of human cytomegalovirus amplicons by sandwich hybridization" Analytical Biochemistry 253:180-189.

International Preliminary Eamination Report from co-pending PCT/BE01/00053 dated Mar. 17, 2003, which claims priority to the same European applications as the above-identified application.

Remacle et al. U.S. Appl. No. 10/056,229, filed Jan. 23, 2002, entitled "Identification of a large number of biological (micro)organisms groups at different levels by their detection on a same array" (Listed, but not enclosed).

Office Action from co-pending U.S. Appl. No. 10/056,229, dated Feb. 25, 2003.

Office Action from co-pending U.S. Appl. No. 10/056,229, dated Jan. 2, 2004.

Letter from Jose Remacle to Eric Van Malderen, dated Feb. 24, 2000.

Guschin et al. (1997) "Oligonucleotide microchips as genosensors for determinative and environmental studies in microbiology" *Appl. Environ. Microbiol.* 63:2397-2402.

Martineau et al. (2000) "Correlation between the resistance genotype determined by multiplex PCR assays and the antibiotic susceptibility patterns of *Staphyl9ococcus aureus* and *Staphylococcus epidermidis*" Antimicrob. Agents Chemother. 44:231-238.

Yershov et al. (1996) "DNA analysis and diagnostics on oligonucleotide microchips" *PNAS USA* 93:4913-4918.

\* cited by examiner

Ctl + fixation
Ctl + hybridation
Ctl - Hybridation
S. aureus
S. epidermidis
S. haemolyticus
S. hominis
S. saprophyticus
Consensus
mecA
Ctl + fixation

FIG. 2

IDENTIFICATION OF BIOLOGICAL (MICRO) ORGANISMS BY DETECTION OF THEIR HOMOLOGOUS NUCLEOTIDE SEQUENCES ON ARRAYS

CROSS-REFERENCE TO RELATED APPLICATION

This application claims priority to European Application Serial Number 00870055.1 filed on Mar. 24, 2000, and European Application Serial Number 00870204.5 filed on Sep. 15, 2000, the disclosures of which are incorporated herein by reference in their entireties.

FIELD OF THE INVENTION

The present invention is in the field of diagnosis and is related to a method and kit comprising reagents and agents for the identification (detection and/or quantification) of (micro)organisms among other ones having homologous nucleotide sequences by identification of their nucleotide sequences, after amplification by a single primer pair.

The invention is especially suited for the identification and/or quantification of (micro)organisms of the same genus or family or for the detection and/or quantification of related genes in a specific (micro)organism present in a biological sample.

BACKGROUND OF THE INVENTION

The development of the biochips technology allows the detection of multiple nucleotide sequences simultaneously in a given assay and thus allow the identification of the corresponding organism or part of the organism. Arrays are solid supports containing on their surface a series of discrete regions bearing capture nucleotide sequences (or probes) that are able to bind (by hybridisation) to a corresponding target nucleotide sequence(s) possibly present in a sample to be analysed. If the target sequence is labelled with modified nucleotides during a reverse transcription or an amplification of said sequence, then a signal can be detected and measured at the binding location. Its intensity gives an estimation of the amount of target sequences present in the sample. Such technology allows the identification and/or quantification of genes or species for diagnostic or screening purpose.

DESCRIPTION OF THE RELATED ART

The Company Affymetrix Inc. has developed a method for direct synthesis of oligonucleotides upon a solid support, at specific locations by using masks at each step of the processing. Said method comprises the addition of a new nucleotide on a growing oligonucleotide in order to obtain a desired sequence at a desired location. This method is derived from the photolithographic technology and is coupled with the use of photoprotective groups, which are released before a new nucleotide is added (EP-A1-0476014, U.S. Pat. No. 5,445,934, U.S. Pat. No. 5,143,854 and U.S. Pat. No. 5,510,270). However, only small oligonucleotides are present on the surface, and said method finds applications mainly for sequencing or identifying a pattern of positive spots corresponding to each specific oligonucleotide bound on the array. The characterization of a target sequence is obtained by comparison of such pattern with a reference. Said technique was applied to the identification of *Mycobacterium tuberculosis* rpoB gene (WO97/29212 and WO98/28444), wherein the capture nucleotide sequence comprises less than 30 nucleotides and from the analysis of two different sequences that may differ by a single nucleotide (the identification of SNPs or genotyping). Small capture nucleotide sequences (having a length comprised between 10 and 20 nucleotides) are preferred since the discrimination between two oligonucleotides differing in one base is higher, when their length is smaller.

The lack of sensitivity of the method is illustrated by the fact that it cannot detect directly amplicons resulting from genetic amplification (PCR). A double amplification with primer(s) bearing a T3 or T7 sequence and then a reverse transcription with an RNA polymerase. These RNA are cut into pieces of about 40 bases before being detected on an array (example 1 of WO 97/29212). However, long DNA or RNA fragments hybridize very slowly on capture probes present on a surface. Said methods are therefore not suited for the detection of homologous sequences since the homology varies along the sequences and so part of the pieces could hybridize on the same capture probes. Therefore, a software for the interpretation of the results should be incorporated in the method for allowing interpretation of the obtained data.

However, for gene expression array which is based on the cDNA copy of mRNA the same problem is encountered when using small capture probe arrays: the rate of hybridisation is low. Therefore, the fragments are cut into smaller species and the method requires the use of several capture nucleotide sequences in order to obtain a pattern of signals which attest the presence of a given gene (WO97/10364 and WO97/27317). Said cutting also decreases the number of labelled nucleotides, and thus reduces the obtained signal. In this case, the use of long capture nucleotide sequences give a much better sensitivity to the detection. In the many gene expression applications, the use of long capture probes is not a problem, when cDNA to be detected originates from genes having different sequences, since there is no cross-reactions between them. Long capture nucleotide sequences give the required sensitivity, however, they will hybridize to other homologous sequences.

Using membranes or nylon supports are proposed to increase the sensitivity of the detection on solid support by incorporation of a spacer between the support and the capture nucleotide sequences. Van Ness et al. (Nucleic Acids Research, Vol. 19, p. 3345, 1991) describe a poly(ethyleneimine) arm for the binding of DNA on nylon membranes. The European patent application EP-0511559 describes a hexaethylene glycol dervivative as spacer for the binding of small oligonucleotides upon a membrane. When membranes like nylon are used as support, there is no control of the site of binding between the solid support and the oligonucleotides and it was observed that a poly dT tail increased the fixation yield and so the resulting hybridization (WO89/11548). Similar results are obtained with repeated capture sequences present in a polymer (U.S. Pat. No. 5,683,872).

Guo et al. (Nucleic Acids Research 22, 5456, 1994) teach the use of poly dT of 15 bases as spacer for the binding of oligonucleotides on glass with increased sensitivity of hybridization.

The document WO99/16780 describes the detection of 4 homologous sequences of the gene femA on nylon strips. However, no data on the sensitivity of the method and the detection is presented. In said document, the capture nucleotide sequences comprise between 15 and 350 bases with homology less than 50% with a consensus sequence.

The publication of Anthony et al. (Journal of clinical microbiology, Vol. 38 nr.2, p. 7817–8820) describes the use of a membrane array for the discrimination with low sensitivity of homologous sequences originated from a several related organisms. Targets to detect are rDNA amplified from bacteria by consensus PCR and the detection is obtained on nylon array containing capture nucleotide sequences for said bacteria and having the capture nucleotide sequences having between 20 and 30 bases which are covalently linked to the nylon, and there is no control of the portion of the sequence which is available for hybridization.

SUMMARY OF THE INVENTION

The present invention aims to provide a new method and device to improve microarrays or biochips technology for the easy identification (detection and/or quantification) of a large number of (micro)organisms or portions of (micro)organisms having homologous nucleotide sequences.

A further aim of the invention is to provide such method and device which are based upon a simplified technology requiring the use of a single primer(s) in an amplification step and which allow the identification (detection and/or quantification) of a sequence target sequence by the identification and/or recording of a single spot signal upon said microarray, said signal resulting only from the specific binding of the target sequence with its corresponding capture sequence.

BRIEF DESCRIPTION OF THE DRAWINGS

FIG. 2 represents the design of an array which allows the determination of the 5 most common *Staphylococcus* species, of the presence of any *Staphylococcus* strain and of the MecA gene.

DETAILED DESCRIPTION OF THE PREFERRED EMBODIMENT

Figure 1:
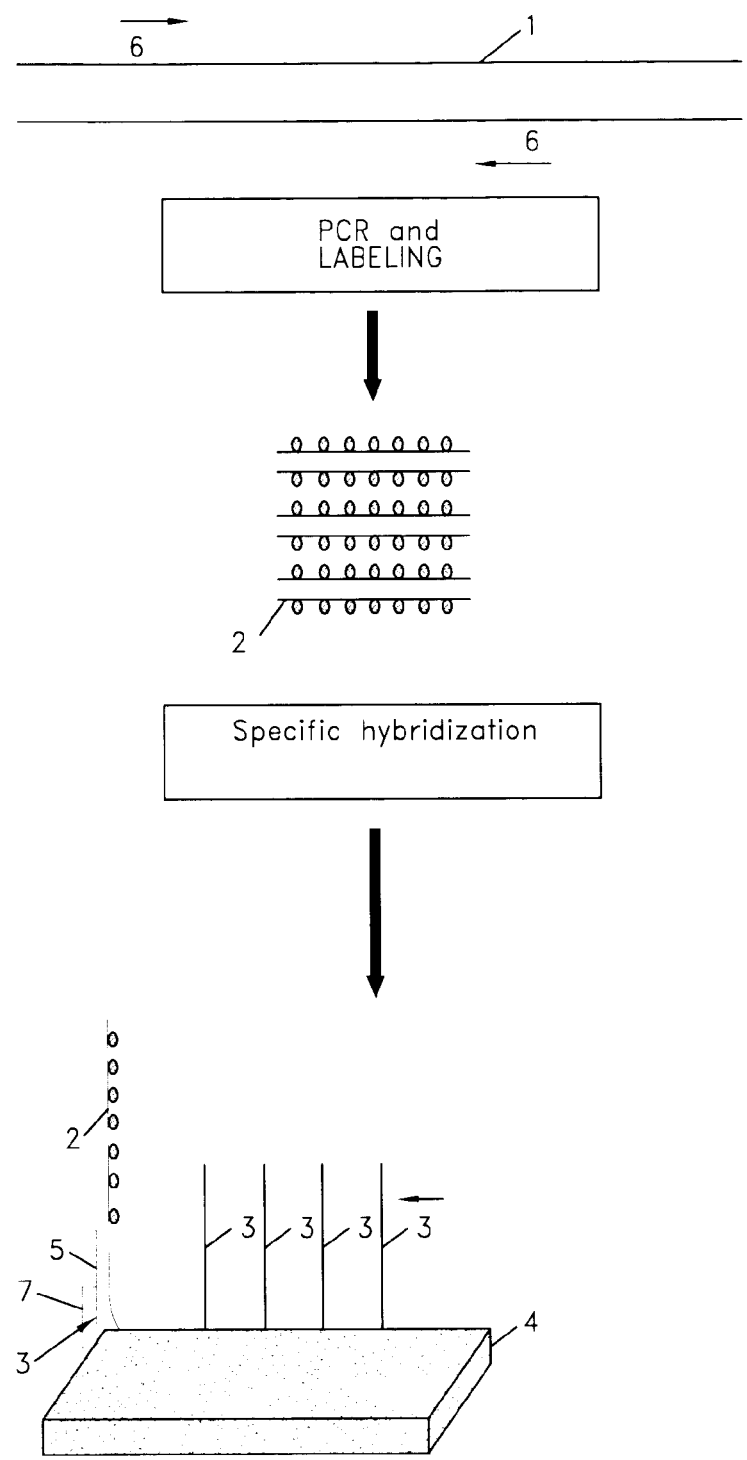
FIG. 1 is a schematic presentation of the step used in the method of the invention for the identification of 5 *Staphylococcus* species on biochips after PCR amplification with consensus primers.

The inventors have discovered that it is possible to drastically simplify the identification of one or several (micro)organisms among many other ones having homologous sequences by combining a single amplification using common primer pair and an identification of the possible (micro)organism(s) by detecting and possibly recording upon an array the presence of a single signal resulting only from a binding between a capture sequence and its corresponding target sequence and correlating the presence of said detected target sequence to the identification of a genetic sequence specific of said (micro)organisms). This means that the method and device according to the invention will allow the easy identification/detection of a specific sequence among other homologous sequences and its quantification (characterisation of the number of copies or presence of said organisms in a biological sample) of a target sequence, said target sequence having a nucleotide sequence specific of said (micro)organisms.

Such identification may be obtained directly, after washing of possible contaminants (unbound sequences), by detecting and possibly recording a single spot signal at one specific location, wherein said capture nucleotide sequence was previously bound and said identification is not a result of an analysis of a specific pattern upon the microarray as proposed in the system of the state of the art. Therefore, said method and device do not necessarily need a detailed analysis of said pattern by an image processing and a software analysis.

This invention was made possible by discovering that target sequences can be discriminated from other homologous ones upon an array with high sensitivity by using bound capture nucleotide sequences composed of at least two parts, one being a spacer bound by a single advantageously predetermined (defined) link to the support (preferably a non porous support) and the other part being a specific nucleotide sequence able to hybridise with the nucleotide target sequence.

Furthermore, said detection is greatly increased, if high concentrations of capture nucleotide sequences are bound to the surface of the solid support.

The present invention is related to the identification of a target sequence obtained from a biological (micro)organism or a portion thereof, especially a gene possibly present in a biological sample from at least 4 other homologous (micro)organisms or a portion thereof, said other (micro)organisms could be present in the same biological sample and have homologous nucleotide sequences with the target.

Said identification is obtained firstly by a genetic amplification of said nucleotide sequences (target and homologous sequences) by common primer pairs followed (after washing) by a discrimination between the possible different target amplified. Said discrimination is advantageously obtained by hybridization upon the surface of an array containing capture nucleotide sequences at a given location, specific for a target specific for each (micro)organism to be possibly present in the biological sample and by the identification of said specific target through the identification and possibly the recording of a signal resulting from the specific binding of this target upon its corresponding capture sequence at the expected location (single location signal being specific for the target).

According to the invention, the preferred method for genetic amplification is the PCR using two anti-parallel consensus primers which can recognise all said target homologous nucleotide sequences.

The method according to the invention further comprises the step of correlating the signal of detection (possibly recorded) to the presence of:

specific (micro)organism(s),
genetic characteristics of a sequence,
polymorphism of a sequence,
diagnostic predisposition or evolution (monitoring) of genetic diseases, including cancer of a patient (including the human) from which the biological sample has been obtained.

Therefore, said (micro)organisms could be present in any biological material including genetic material obtained (virus, fungi, bacteria, plant or animal cell, including the human). The biological sample can be also any culture medium wherein microorganisms, xenobiotics or pollutants are present, as well as such extract obtained from a plant or an animal (including a human) organ, tissue, cell or biological fluid (blood, serum, urine, etc).

The method according to the invention can be performed by using a specific identification (diagnostic and/or quantification) kit or device comprising at least an insoluble solid support upon which are bound single-stranded capture nucleotide sequences (preferably bound to the surface of the solid support by a direct covalent link or by the intermediate of a spacer) according to an array with a density of at least 4, preferably at least 10, 16, 20, 50, 100, 1000, 4000, 10 000 or more, different single-stranded capture nucleotide sequences/cm$^2$ insoluble solid support surface, said single-stranded capture nucleotide sequences having advantageously a length comprised between about 30 and about 600 bases (including the spacer) and containing a sequence of about 10 to about 60 bases, said sequence being specific for the target (which means that said bases of said sequence are able to form a binding with their complementary bases upon the sequence of the target by complementary hybridisation). Preferably, said hybridisation is obtained under stringent conditions (under conditions well-known to the person skilled in the art).

In the method and kit or device according to the invention, the capture nucleotide sequence is a sequence having between 16 and 600 bases, preferably between 30 and 300 bases, more preferably between 40 and 150 bases and the spacer is a chemical chain of at least 6.8 nm long (of at least 4 carbon chains), a nucleotide sequence of more than 30 bases or is nucleotide derivative such as PMA.

The method, kit and device according to the invention are particularly suitable for the identification of a target, being preferably biological (micro)organisms or a part of it, possibly present in a biological sample where at least 4, 12, 15 or even more homologous sequences are present. Because of the high homology, said sequence can be amplified by common primer(s) so that the identification of the target is obtained specifically by the discrimination following its binding with the corresponding capture nucleotide sequence, previously bound at a given location upon the microarray. The sensitivity can be also greater increased if capture nucleotide sequences are spotted to the solid support surface by a robot at high density according to an array. A preferred embodiment of the invention is to use an amount of capture nucleotide sequences spotted on the array resulting in the binding of between about 0.01 to about 5 pmoles of sequence equivalent/cm$^2$ of solid support surface.

The kit or device according to the invention may also incorporate various media for performing the method according to the invention. Said kit (or device) can also be included in an automatic apparatus such as a high throughput screening apparatus for the detection and/or the quantification of multiple nucleotide sequences present in a biological sample to be analysed. Said kit or apparatus can be adapted for performing all the steps or only several specific steps of the method according to the invention.

In the method, the kit (device) or apparatus according to the invention, the length of the bound capture nucleotide sequences is preferably comprised between about 30 and about 600 bases, preferably between about 40 and about 400 bases and more preferably between about 40 and about 100 bases. Longer nucleotide sequences can be used if they do not lower the binding yield of the target nucleotide sequences usually by adopting hairpin based secondary structure or by interaction with each other.

If the homology between the sequences to be detected is low (between 30 and 60%), parts of the sequence which are specific in each sequence can be used for the design of specific capture nucleotide sequences binding each of the different target sequences. However, it is more difficult to find part of the sequence sufficiently conserved as to design "consensus" sequences which will amplify or copy all desired sequences. If one pair of consensus primers is not enough to amplify all the homologous sequences, then a mixture of two or more primers pairs is added in order to obtain the desired amplifications. The minimum homologous sequences amplified by the same consensus primer is two, but there is no limitation to said number.

If the sequences show high degree of homology, higher than 60% and even higher than 90%, then the finding of common sequence for consensus primer is easily obtained, but the choice for specific capture nucleotide sequences become more difficult.

In another preferred embodiment of the invention, the capture nucleotide sequences are chemically synthesised oligonucleotides sequences shorter than 100 bases (easily performed on programmed automatic synthesiser). Such sequences can bear a functionalised group for covalent attachment upon the support, at high concentrations.

Longer capture nucleotide sequences are preferably synthesised by PCR amplification (of a sequence incorporated into a plasmid containing the specific part of the capture nucleotide sequence and the non specific part (spacer)).

In a further embodiment of the invention, the specific sequence of the capture nucleotide sequence is separated from the surface of the solid support by at least about 6.8 nm long, equivalent to the distance of at least 20 base pair long nucleotides in double helix form.

In the method, kit (device) or apparatus according to the invention, the portion(s) (or part(ies)) of the capture nucleotide sequences complementary to the target is comprised between about 10 and about 60 bases, preferably between about 15 and about 40 bases and more preferably between about 20 and about 30 bases. These bases are preferably assigned as a continuous sequence located at or near the extremity of the capture nucleotide sequence. This sequence is considered as the specific sequence for the detection. In a preferred form of the invention, the sequence located between the specific capture nucleotide sequence and the support is a non specific sequence.

In another embodiment of the invention, a specific nucleotide sequence comprising between about 10 and about 60 bases, preferably between about 15 and about 40 bases and more preferably between about 20 and about 30 bases is located on a capture nucleotide sequence comprising a sequence between about 30 and about 600 bases.

The method, kit (device) or apparatus according to the invention are suitable for the detection and/or the quantification of a target which is made of DNA or RNA, including sequences which are partially or totally homologous upon their total length.

The method according to the invention can be performed even when a homology (or sequence identity) between a target present and other molecules is greater than 30%, greater than 60% and even greater than 80%.

In the method, kit (device) or apparatus according to the invention, the capture nucleotide sequences are advantageously covalently bound (or fixed) upon the insoluble solid support, preferably by one of their extremities as described hereafter.

The method according to the invention gives significant results which allows identification (detection and quantification) with amplicons in solutions at concentration of lower than about 10 nM, of lower than about 1 nM, preferably of lower than about 0.1 nM and more preferably of lower than about 0.01 nM (=1 fmole/100 µl).

Another important aspect of this invention is to use a high concentration of capture nucleotide sequences on the surface. If the concentration too is low, the yield of the binding is lower and is undetectable. Concentrations of capture nucleotide sequences between about 100 and about 3,000 nM in the spotting solutions are preferred. However, concentrations as low as about 100 nM still give positive results in favourable cases (when the yield of covalent fixation is high or when the target to be detected is single-stranded and present in high concentrations). Such low spotting concentrations would give density of capture nucleotide sequence as low as 20 fmoles per $cm^2$. On the other side, higher density was only limited in the assays by the concentrations of the capture solutions, but concentrations still higher than 3,000 nM give good results.

The use of these very high concentrations and long probes are two unexpected characteristic features of the invention. The theory of DNA hybridisation proposed that the rate of hybridisation between two DNA complementary sequences in solution is proportional to the square root of the DNA length, the smaller one being the limiting factor (Wetmur, J. G. and Davidson, N. 1968, J. Mol. Biol. 3, 584). In order to obtain the required specificity, the specific sequences of the capture nucleotide sequences had to be smaller compared to the target. Moreover, the targets were obtained after PCR amplification and were double-stranded so that they reassociate in solution much faster than to be small sequences fixed on a solid support where diffusion is low thus reducing even more the rate of reaction. It was unexpected to observe a so large increase in the yield of hybridisation with the same short specific sequence.

The amount of a target which "binds" on the spots is very small compared to the amount of capture nucleotide sequences present. So there is a large excess of capture nucleotide sequence and there was no reason to obtain the binding with even more capture nucleotide sequences.

One may perform the detection on the full length sequence after amplification or copy and when labelling is performed by incorporation of labelled nucleotides, more markers are present on the hybridised target making the assay sensitive.

The method, kit and apparatus according to the invention may comprise the use of other bound capture nucleotide sequences, which may have the same characteristics as the previous ones and may be used to identifying a target from another group of homologous sequences (preferably amplified by common primer(s)).

In the microbiological field, one may use consensus primer(s) specific for each family, or genus, of microorganisms and then identify some or all the species of these various family in an array by using capture nucleotide sequences of the invention. Detection of other sequences can be advantageously performed on the same array (i.e. by allowing an hybridisation with a standard nucleotide sequence used for the quantification, with consensus capture nucleotide sequences for the same or different micro-organisms strains, with a sequence allowing a detection of a possible antibiotic resistance gene by micro-organisms or for positive or negative control of hybridisation). Said other capture nucleotide sequences have (possibly) a specific sequence longer than 10 to 60 bases and a total length as high as 600 bases and are also bound upon the insoluble solid support (preferably in the array made with the other bound capture nucleotide sequences related to the invention). A long capture nucleotide sequence may also be present on the array as consensus capture nucleotide sequence for hybridisation with all sequences of the microorganisms from the same family or genus, thus giving the information on the presence or not of a microorganism of such family, genus in the biological sample.

The same array can also bear capture nucleotide sequences specific for a bacterial group (Gram positive or Gram negative strains or even all the bacteria).

Another application is the detection of homologous genes from a consensus protein of the same species, such as various cytochromes P450 by specific capture nucleotide sequences with or without the presence of a consensus capture nucleotide sequence for all the cytochromes possibly present in a biological sample. Such detection is performed at the gene level by reverse transcription into cDNA.

The solid support according to the invention can be or can be made with materials selected from the group consisting of gel layers, glasses, electronic devices, silicon or plastic support, polymers, compact discs, metallic supports or a mixture thereof (see EP 0 535 242, U.S. Pat. No. 5,736,257, WO99/35499, U.S. Pat. No. 5,552,270, etc). Advantageously, said solid support is a single glass slide which may comprise additional means (barcodes, markers, etc.) or media for improving the method according to the invention.

The amplification step used in the method according to the invention is advantageously obtained by well known amplification protocols, preferably selected from the group consisting of PCR, RT-PCR, LCR, CPT, NASBA, ICR or Avalanche DNA techniques.

Advantageously, the target to be identified is labelled prior to its hybridisation to the single-stranded capture nucleotide sequences. Said labelling (with known techniques from the person skilled in the art) is preferably also obtained upon the amplified sequence prior to the denaturation (if the method includes an amplification step).

Advantageously, the length of the target is selected as being of a limited length preferably between 100 and 200 bases, preferably between 100 and 400 bases and more preferably between 100 and 800 bases. This preferred requirement depends on the possibility to find consensus primers to amplify the required sequences possibly present in the sample. Too long target may reallocate faster and adopt secondary structures which can inhibit the fixation on the capture nucleotide sequences.

Detection of genes is also a preferred application of this invention. The detection of homologous genes is obtained by first reverse transcription of the mRNA and then amplification by consensus primers as described in this invention.

According to a further aspect of the present invention, the method, kit (device) or apparatus according to the invention is advantageously used for the identification of different *Staphylococcus* species or variants, preferably the *S. aureus*, the *S. epidermidis*, the *S. saprophyticus*, the *S. hominis* or the *S. haemolyticus* for homologous organisms present together or separately in the biological sample, said identification being obtained by detecting the genetic variants of the FemA gene in said different species, preferably by using a common location in the FemA genetic sequence.

Preferably, the primer(s) and the specific portions of said FemA sequence used for obtaining amplified products are the ones described hereafter in example 2. These primers have been selected as consensus primers for the amplification of the FemA genes of all of the 16 *Staphylococcus* tested and they probably will amplify the FemA from all other possible *Staphylococcus* species.

The detection of the 12 MAGE according to the invention is presented in example 9. The array allows to read the MAGE number by observation of the lines positive for signal bearing the specific capture probes.

The same application was developed for the Receptors Coupled to the G Proteins (RCGP). These receptors bind all sort of ligands and are responsible for the signal transduction to the cytoplasm and very often to the nucleus by modulating the activity of the transcriptional factors. Consensus primers are formed for the various subtypes of RCGP for dopamine and for serotonine and histamine (examples 10–12). The same is possible for the histamine and other ligands.

The detection of the various HLA types is also one of the applications of the invention (example 13). HLA are homologous sequences which differ from one individual to the other. The determination of the HLA type is especially useful in tissue transplantation in order to determine the degree of compatibility between the donor and the recipient. It is also a useful parameter for immunisation. Given the large number of subtypes and the close relation between the homologous sequences it was not always possible to perfectly discriminate one sequence among all the other ones and for some of them there was one or two cross-reactions. In these cases, another capture probe was added on the array which gives a reaction with the sequence to be detected and another cross-reaction, in order to make the identification absolute.

There are several forms of Cytochrome P450 which are also homologous sequences. Example 14 presents the design of the array to identify several cytochromes P450 after reverse transcription and amplification with consensus primers.

The detection of polymorphism sequences (which can be considered as homologous even if differing by only one base) can be made also by the method according to the invention. This is especially useful for the Cytochrome P450 since the presence of certain isoforms modifies the metabolism of some drugs.

Another aspect of the present invention is related to any part of biochips or microarray comprising said above described sequences (especially the specific capture nucleotide sequence described in the examples) as well as a general screening method for the identification of a target sequence specific of said microorganisms of family type discriminated from homologous sequences upon any type of microarrays or biochips by any method.

After hybridisation on the array, the target sequences can be detected by current techniques. Without labelling, preferred methods are the identification of the target by mass spectrometry now adapted to the arrays (U.S. Pat. No. 5,821,060) or by intercalating agents followed by fluorescent detection (WO97/27329 or Fodor et al., Nature 364, p. 555 (1993)).

The labelled associated detections are numerous. A review of the different labelling molecules is given in WO 97/27317. They are obtained using either already labelled primer or by incorporation of labelled nucleotides during the copy or amplification step. A labelling can also be obtained by ligating a detectable moiety onto the RNA or DNA to be tested (a labelled oligonucleotide, which is ligated, at the end of the sequence by a ligase). Fragments of RNA or DNA can also incorporate labelled nucleotides at their 5'OH or 3'OH ends using a kinase, a transferase or a similar enzyme.

The most frequently used labels are fluorochromes like Cy3, Cy5 and Cy7 suitable for analysing an array by using commercially available array scanners (General Scanning, Genetic Microsystem). Radioactive labelling, cold labelling or indirect labelling with small molecules recognised thereafter by specific ligands (streptavidin or antibodies) are common methods. The resulting signal of target fixation on the array is either fluorescent, colorimetric, diffusion, electroluminescent, bio- or chemiluminescent, magnetic, electric like impedometric or voltametric (U.S. Pat. No. 5,312,527). A preferred method is based upon the use of the gold labelling of the bound target in order to obtain a precipitate or silver staining which is then easily detected and quantified by a scanner.

Quantification has to take into account not only the hybridisation yield and detection scale on the array (which is identical for target and reference sequences) but also the extraction, the amplification (or copying) and the labelling steps.

The method according to the invention may also comprise means for obtaining a quantification of target nucleotide sequences by using a standard nucleotide sequence (external or internal standard) added at known concentration. A capture nucleotide sequence is also present on the array so as to fix the standard in the same conditions as said target (possibly after amplification or copying); the method comprising the step of quantification of a signal resulting from the formation of a double stranded nucleotide sequence formed by complementary base pairing between the capture nucleotide sequences and the standard and the step of a correlation analysis of signal resulting from the formation of said double-stranded nucleotide sequence with the signal resulting from the double stranded nucleotide sequence formed by complementary base pairing between capture nucleotide sequence(s) and the target in order to quantify the presence of the original nucleotide sequence to be detected and/or quantified in the biological sample.

Advantageously the standard is added to the initial biological sample or after the extraction step and is amplified or copied with the same primers and/or has a length and a GC content identical or differing by no more than 20% from the target. More preferably, the standard can be designed as a competitive internal standard having the characteristics of the internal standard found in the document WO98/11253. Said internal standard has a part of its sequence common to the target and a specific part which is different. It also has at or near its two ends sequences which are complementary of the two primers used for amplification or copy of the target and similar GC content (WO98/11253). In the preferred embodiment of this invention, the common part of the standard and the target, means a nucleotide sequence which is homologous to all target amplified by the same primers (i.e. which belong to the same family or organisms to be quantified).

Preferably, the hybridisation yield of the standard through this specific sequence is identical or differ no more than 20% from the hybridisation yield of the target sequence and quantification is obtained as described in WO 98/11253.

Said standard nucleotide sequence, external and/or internal standard, is also advantageously included in the kit (device) or apparatus according to the invention, possibly with all the media and means necessary for performing the different steps according to the invention (hybridisation and culture media, polymerase and other enzymes, standard sequences(s), labelling molecule(s), etc.).

Advantageously, the biochips also contain spots with various concentration (i.e. 4) of labelled capture nucleotide sequences. These labelled capture nucleotide sequences are spotted from known concentrations solutions and their signals allow the conversion of the results of hybridisation into absolute amounts. They also allow to test for the reproducibility of the detection.

The solid support (biochip) can be inserted in a support connected to another chamber and automatic machine through the control of liquid solution based upon the use of microfluidic technology. By being inserted into such a microlaboratory system, it can be incubated, heated, washed and labelled by automates, even for previous steps (like extraction of DNA, amplification by PCR) or the following step (labelling and detection). All these steps can be performed upon the same solid support.

The present invention will be described in details in the following non-limiting examples in reference to the enclosed figures.

EXAMPLES

Example 1

Detection of Homologous FemA Sequences on Array Bearing Long Specific Capture Nucleotide Sequences Production of the Capture Nucleotide Sequences and of the Targets The FemA genes corresponding to the different *Staphylococci* species were amplified separately by PCR using the following primers:

```
                                        (SEQ ID NO: 1)
S. aureus 1:       5' CTTTTGCTGATCGTGATGACAAA 3'

(SEQ ID NO: 2)
S. aureus 2:       5' TTTATTTAAAATATCACGCTCTTCG 3'

(SEQ ID NO: 3)
S. epidermidis 1:  5' TCGCGGTCCAGTAATAGATTATA 3'

(SEQ ID NO: 4)
S. epidermidis 2:  5' TGCATTTCCAGTTATTTCTCCC 3'

(SEQ ID NO: 5)
S. haemolyticus 1: 5' ATTGATCATGGTATTGATAGATAC 3'

(SEQ ID NO: 6)
S. haemolyticus 2: 5' TTTAATCTTTTTGAGTGTCTTATAC 3'

(SEQ ID NO: 7)
S. saprophyticus 1: 5' TAAAATGAAACAACTCGGTTATAAG 3'

(SEQ ID NO: 8)
S. saprophyticus 2: 5' AAACTATCCATACCATTAAGTACG 3'

(SEQ ID NO: 9)
S. hominis 1:      5' CGACCAGATAACAAAAAAGCACAA 3'

(SEQ ID NO: 10)
S. hominis 2:      5' GTAATTCGTTACCATGTTCTAA 3'
```

The PCR was performed in a final volume of 50 μl containing: 1.5 mM MgCl$_2$, 10 mM Tris pH 8.4, 50 mM KCl, 0.8 μM of each primer, 50 μM of each dNTP, 50 μM of biotin-16-dUTP), 1.5 U of Taq DNA polymerase Biotools, 7.5% DMSO, 5 ng of plasmid containing FemA gene. Samples were first denatured at 94° C. for 3 min. Then 40 cycles of amplification were performed consisting of 30 sec at 94° C., 30 sec at 60° C. and 30 sec at 72° C. and a final extension step of 10 min at 72° C. Water controls were used as negative controls of the amplification. The sizes of the amplicons obtained using these primers were 108 bp for *S. saprophyticus*, 139 bp for *S. aureus*, 118 bp for *S. hominis*, 101 bp for *S. epidermidis* and 128 bp for *S. haemolyticus*. The sequences of the capture nucleotide sequences were the same as the corresponding amplicons but they were single strands.

The biochips also contains positive controls which were CMV amplicons hybridised on their corresponding capture nucleotide sequence and negative controls which were capture nucleotide sequences for a HIV-I sequence on which the CMV could not bind.

Capture Nucleotide Sequence Immobilisation

The protocol described by Schena et al (Proc. Natl. Acad. Sci. USA 93, 10614 (1996)) was followed for the grafting of aminated DNA to aldehyde derivatised glass. The aminated capture nucleotide sequences were spotted from solutions at concentrations ranging from 150 to 3000 nM. The capture nucleotide sequences were printed onto the silylated microscopic slides with a home made robotic device (250 μm pins from Genetix (UK) and silylated (aldehyde) microscope slides from Cell associates (Houston, USA)). The spots have 400 μm in diameter and the volume dispensed is about 0.5 nl. Slides were dried at room temperature and stored at 4° C. until used.

Hybridisation

At 65 μl of hybridisation solution (AAT, Namur, Belgium) were added 5 μl of amplicons and the solution was loaded on the array framed by an hybridisation chamber. For positive controls we added 2 nM biotinylated CMV amplicons of 437 bp to the solution; their corresponding capture nucleotide sequences were spotted on the array. The chamber was closed with a covership and slides were denatured at 95° C. for 5 min. The hybridisation was carried out at 60° for 2 h. Samples were washed 4 times with a washing buffer.

Colorimetric Detection

The glass samples were incubated 45 min at room temperature with 800 μl of streptavidin labelled with colloidal gold 1000× diluted in blocking buffer (Maleic buffer 100 mM pH 7.5, NaCl 150 mM, Gloria milk powder 0.1%). After 5 washes with washing buffer, the presence of gold served for catalysis of silver reduction using a staining revelation solution (AAT, Namur, Belgium). The slides were incubated 3 times 10 min with 800 μl of revelation mixture, then rinsed with water, dried and analysed using a microarray reader. Each slides were then quantified by a specific quantification software.

Fluorescence Detection

The glass samples were incubated 45 min at room temperature with 800 μl of Cyanin 3 or Cyanin 5 labelled streptavidin. After washing the slides were dried before being stored at room temperature. The detection was performed in the array-scanner GSM 418 (Genetic Microsystem, Woburn, Mass., USA). Each slide was then quantified by a specific quantification software.

The results give a cross-reaction between the species. For example, *epidermidis* amplicons hybridised on its capture probe give a value of 152, but give a value of 144, 9, 13 and 20 respectively for the *S. saprophyticus, S. aureus, S. haemolyticus* and *S. hominis* capture probes.

Example 2

Detection of Homologous FemA Sequences on Array Bearing Small Specific Capture Nucleotide Sequences Protocols for capture nucleotide sequences immobilisation and silver staining detection were described in example 1 but the capture nucleotide sequences specific of the 5 *Staphylococcus* species were spotted at concentrations of 600 nM and are the following:

| Name Capture nucleotide sequence | Sequence (5' -> 3') |
|---|---|
| ATaur02 | ATTTAAAATATCACGCTCTTCGTTTAG (SEQ ID NO: 11) |
| ATepi02 | ATTAAGCACATTTCTTTCATTATTTAG (SEQ ID NO: 12) |
| Athae02 | ATTTAAAGTTTCACGTTCATTTTGTAA (SEQ ID NO: 13) |
| AThom02 | ATTTAATGTCTGACGTTCTGCATGAAG (SEQ ID NO: 14) |
| ATsap02 | ACTTAATACTTCGCGTTCAGCCTTTAA (SEQ ID NO: 15) |

In this case, the targets are fragments of the FemA gene sequence corresponding to the different *Staphylococci* species which were amplified by a PCR using the following consensus primers:

APstap03: 5' CCCACTCGCTTATATAGAATTTGA 3' (SEQ ID NO: 16)

APstap04: 5' CCACTAGCGTACATCAATTTTGA 3' (SEQ ID NO: 17)

APstap05: 5' GGTTTAATAAAGTCACCAACATATT 3' (SEQ ID NO: 18)

Figure 4:
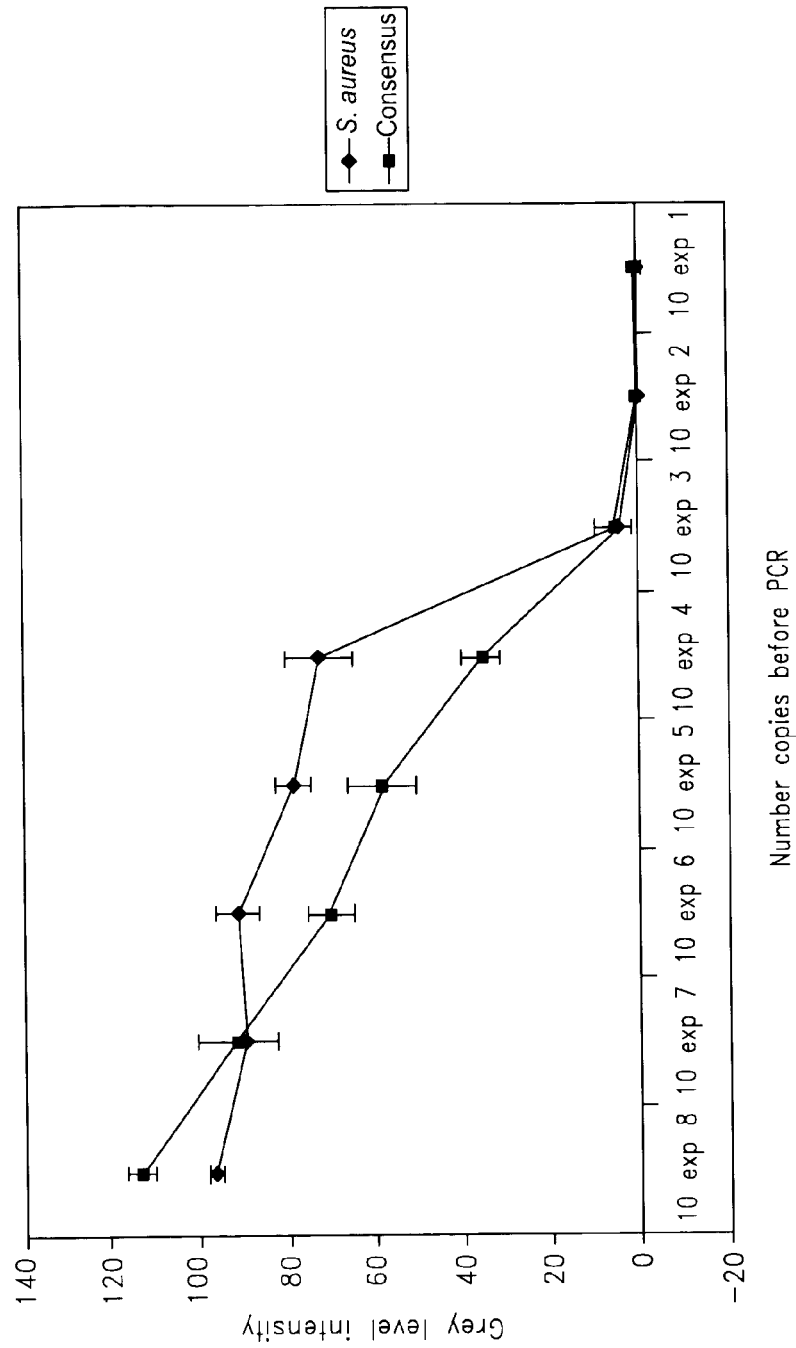
FIG. 4 shows the sensitivity obtained for the detection of FemA sequences from *S. aureus* on array bearing the small specific capture nucleotide sequence for a *S. aureus* and a consensus sequence.

This PCR was performed in a final volume of 100 µl containing: 3 mM MgCl$_2$, 1 mM Tris pH 8, 1 µM of each primer, 200 µM of dACTP, dCTP and dGTP, 150 µM of dTTP, 50 µM of biotin-16-dUTP, 2.5 U of Taq DNA polymerase (Boehringer Mannheim, Allemagne), 1 U of Uracil-DNA-glycosylase heat labile (Boehringer Mannheim, Allemagne), 1 ng of plasmid containing FemAA gene. Samples were first denatured at 94° C. for 5 min. Then 40 cycles of amplification were performed consisting of 1 min at 94° C., 1 min at 50° C. and 1 min at 72° C. and a final extension step of 10 min at 72° C. Water controls were used as negative controls of the amplification. The sizes of the amplicons obtained using these primers were 489 bp for all species. FIG. 4 shows only the results obtained with the amplicons for *S. epidermidis* and *S. xylosus*.

The hybridisation solution was prepared as in example 1 and loaded on the slides. Slides were denatured at 98° C. for 5 min. Hybridisation are carried out at 50° C. for 2 h. Samples are then washed 4 times with a washing buffer. The values were very low and almost undetectable.

Example 3

Effect of the Spacer Length on the Sensitivity of Detection of Homologous FemA Sequences on Array Bearing Long Capture Nucleotide Sequences with a Small Specific Sequence The experiment was conducted as described in example 2 with the same amplicons but the capture nucleotide sequences used are the following:

| Name Capture nucleotide sequence | Sequence (5' -> 3') |
|---|---|
| Ataur02 | ATTTAAAATATCACGCTCTTCGTTTAG (SEQ ID NO: 11) |
| ATepi02 | ATTAAGCACATTTCTTTCATTATTTAG (SEQ ID NO: 12) |
| Atepi03 | <u>GAATTCAAAGTTGCTGAGAAA</u>ATTAAGCACATTTCTTTCATTATTTAG (SEQ ID NO: 19) |
| ATepi04 | <u>GAATTCAAAGTTGCTGAGAATAGTTCAATGGAAGGAAGCG</u>ATTAAGCACATTTCTTTCATTATTTAG (SEQ ID NO: 20) |
| ATepi05 | <u>GAATTCAAAGTTGCTGAGAATAGTTCAATGGAAGGAAGCGTCTTCTTAAAATCTAAAGAAA</u>ATTAAGCACATTTCTTTCATTATTTAG (SEQ ID NO: 21) |

[a]The spacer sequences are underlined

Figure 3:
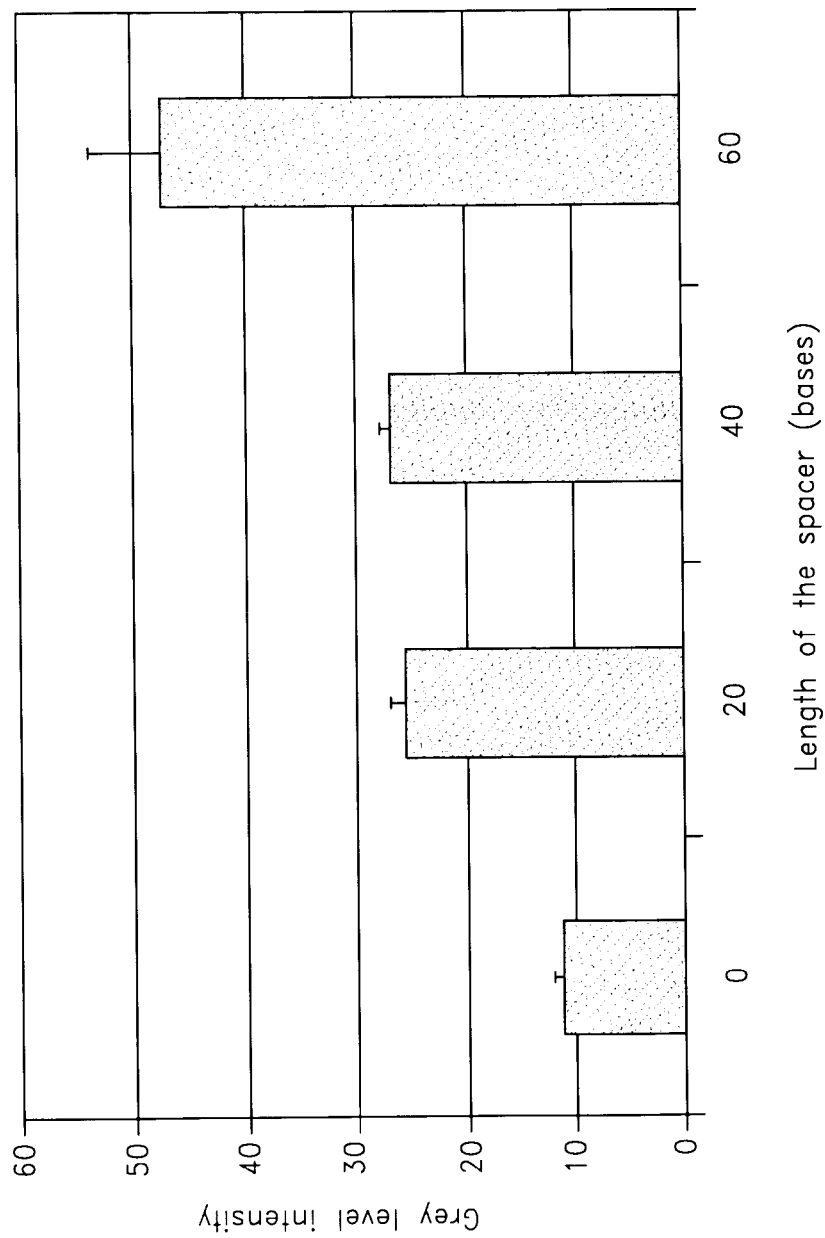
FIG. 3 presents the effect of the length of the spacer sequence of a capture nucleotide sequence on the discrimination between sequences with different level of homology.

The target amplicons were 489 bp long while the capture nucleotide sequences were 47, 67 or 87 bases single-stranded DNA with a specific sequence of 27 bases (FIG. 3).

Example 4

Specificity of the Detection of FemA Sequences from Different Bacterial Species on the Same Array Bearing Long Capture Nucleotide Sequences with a Small Specific Sequence The experiment was conducted as described in example 2 but the capture nucleotide sequences were spotted at concentrations of 3000 nM and are the following:

| Name Capture nucleotide sequence | Sequence (5' -> 3') |
|---|---|
| Ataur27 | <u>GAATTCAAAGTTGCTGAGAATAGTTCAATGGAAGGAAGCG</u>ATTT AAAATATCACGCTCTTCGTTTAG (SEQ ID NO: 22) |
| Atepi27 | <u>GAATTCAAAGTTGCTGAGAATAGTTCAATGGAAGGAAGCG</u>ATTA AGCACATTTCTTTCATTATTTAG (SEQ ID NO: 23) |
| Athae27 | <u>GAATTCAAAGTTGCTGAGAATAGTTCAATGGAAGGAAGCG</u>ATTT AAAGTTTCACGTTCATTTTGTAA (SEQ ID NO: 24) |
| Athom27 | <u>GAATTCAAAGTTGCTGAGAATAGTTCAATGGAAGGAAGCG</u>ATTT AATGTCTGACGTTCTGCATGAAG (SEQ ID NO: 25) |
| Atsap27 | <u>GAATTCAAAGTTGCTGAGAATAGTTCAATGGAAGGAAGCG</u>ACTT AATACTTCGCGTTCAGCCTTTAA (SEQ ID NO: 26) |

<sup>a</sup>The spacer sequence is underlined. The specific sequences were of 27 bases The targets are fragments of the FemA gene sequence corresponding to the different *Staphylococci* species which were amplified by PCR using the following consensus primers:

APcons3-1: 5' TAAYAAARTCACCAACATAYTC 3' (SEQ ID NO: 27)

APcons3-2: 5' TYMGNTCATTTATGGAAGATAC 3' (SEQ ID NO: 28)

A consensus sequence is present on the biochips which detects all the tested *Staphylococci* species. All target sequences were amplified by PCR with the same pair of primers.

The size of the amplicons obtained using these primers were 587 bp for all species. The consensus sequence capture probe was a 489 base long single stranded DNA complementary to the amplicons of *S. hominis* as amplified in example 2. The detection was made in fluorescence. Homology between the consensus capture probe and the sequences of the femA from the 15 S. species were between 66 and 85%. All the sequences hybridized on this consensus capture probe.

Example 5

Effect of the Length of the Specific Sequence of the Capture Nucleotide Sequence on the Discrimination Between Homologous Sequences The experiment was conducted as described in example 4 but at a temperature of 43° C. and the capture nucleotide sequences used are presented in the table here joined. The numbers after the names indicate the length of the specific sequences.

The FemA amplicons of *S. anaerobius* (a subspecies of *S. aureus*) were hybridised on array bearing capture nucleotide sequences of 67 single stranded bases with either 15, 27 and 40 bases specific for the *S. aureus, anaerobius* and *epidermidis* at their extremities. The difference between the capture nucleotide sequences of *anaerobius* and *aureus* was only one base in the 15 base capture nucleotide sequence and 2 in the 27 and the 40 bases.

The amplicons of the FemA from the three *Staphylococcus* species were hybridised on the arrays.

| Name Capture nucleotide sequence | Sequence (5' -> 3') |
|---|---|
| Ataur15 | <u>GAATTCAAAGTTGCTGAGAATAGTTCAATGGAAGGAAGCG</u> <u>TCTTCTTAAAAT</u>GCTCTTCGTTTAGTT (SEQ ID NO: 29) |
| Ataur27 | <u>GAATTCAAAGTTGCTGAGAATAGTTCAATGGAAGGAAGCG</u> ATTTAAAATATCGCTCTTCGTTTAG (SEQ ID NO: 22) |
| Ataur40 | <u>GAATTCAAAGTTGCTGAGAATAGTTCAAATCTTTATTTAAA</u> ATATCACGCTCTTCGTTTAGTTCTTT (SEQ ID NO: 30) |
| Atana15 | <u>GAATTCAAAGTTGCTGAGAATAGTTCAATGGAAGGAAGCG</u> <u>TCTTCTTAAAAT</u>GCTCTTCATTTAGTT (SEQ ID NO: 31) |
| Atana27 | <u>GAATTCAAAGTTGCTGAGAATAGTTCAATGGAAGGAAGCG</u> GTTTAAAATATCACGCTCTTCATTTAG (SEQ ID NO: 32) |

-continued

| Name Capture nucleotide sequence | Sequence (5' -> 3') |
|---|---|
| Atana40 | GAATTCAAAGTTGCTGAGAATAGTTCAAATCTTTGTTTAAA ATATCACGCTCTTCATTTAGTTCTTT (SEQ ID NO: 33) |
| Atepi15 | GAATTCAAAGTTGCTGAGAATAGTTCAATGGAAGGAAGCG TCTTCTTAAAATTTTCATTATTTAGTT (SEQ ID NO: 34) |
| Atepi27 | GAATTCAAAGTTGCTGAGAATAGTTCAATGGAAGGAAGCG ATTAAGCACATTTCTTTCATTATTTAG (SEQ ID NO: 23) |
| Atepi40 | GAATTCAAAGTTGCTGAGAATAGTTCAAATCTTTATTAAG CACATTTCTTTCATTATTTAGTTCCTC (SEQ ID NO: 35) |

Example 6

Sensitivity of the Detection of FemA Sequences of *Staphylococcus Aureus* on Arrays Bearing Specific Sequence as Proposed by this Invention and the Consensus Sequence (FIG. 4)

The experiment was conducted as described in example 4 with the capture nucleotide sequences spotted at concentrations of 3000 nM. The bacterial FemA sequences were serially diluted before the PCR and being incubated with the arrays.

Example 7

Detection of 16 Homologous FemA Sequences on Array

The consensus primers and the amplicons were the same as described in the example 4 but the capture probes were chosen for the identification of 15 *Staphylococcus* species. The experiment is conducted as in example 4. The capture probes contain a spacer fixed on the support by its 5' end and of the following sequence 5' GAATTCAAAGTTGCT-GAGAATAGTTCAATGGAAGGAAGCG 3' (SEQ ID NO: 36) followed by the following specific sequences for the various femA from the different *Staphylococcus*:

| | (SEQ ID NO: 37) |
|---|---|
| S. aureus | ATTTAAAATATCACGCTCTTCGTTTAG |
| | (SEQ ID NO: 38) |
| S. epidermidis | ATTAAGCACATTTCTTTCATTATTTAG |
| | (SEQ ID NO: 39) |
| S. haemolyticus | ATTTAAAGTTTCACGTTCATTTTGTAA |
| | (SEQ ID NO: 40) |
| S. hominis | ATTTAATGTCTGACGTTCTGCATGAAG |
| | (SEQ ID NO: 41) |
| S. saprophyticus | ACTTAATACTTCGCGTTCAGCCTTTAA |
| | (SEQ ID NO: 42) |
| S. capitis | ATTAAGAACATCTCTTTCATTATTAAG |
| | (SEQ ID NO: 43) |
| S. caseolyticus | ATAAAGACATTCGAGACGAAGGCT |
| | (SEQ ID NO: 44) |
| S. cohnii | ACTTAACACTTCACGCTCTGACTTGAG |

| | (SEQ ID NO: 45) |
|---|---|
| S. gallinarum | ACTTAAAACTTCACGTTCAGCAGTAAG |
| | (SEQ ID NO: 46) |
| S. intermedius | GTGGAAATCTTGCTCTTCAGATTTCAG |
| | (SEQ ID NO: 47) |
| S. lugdunensis | TTCTAAAGTTTGTCGTTCATTCGTTAG |
| | (SEQ ID NO: 48) |
| S. schleiferi | TTTAAAGTCTTGCGCTTCAGTGTTGAG |
| | (SEQ ID NO: 49) |
| S. sciuri | GTTGTATTGTTCATGTTCTTTTTCTAA |
| | (SEQ ID NO: 50) |
| S. simulans | TTCTAAATTCTTTTGTTCAGCGTTCAA |
| | (SEQ ID NO: 51) |
| S. warneri | AGTTAAGGTTTCTTTTTCATTATTGAG |
| | (SEQ ID NO: 52) |
| S. xylosus | GCTTAACACCTCACGTTGAGCTTGCAA |

Example 8

Detection of 19 Homogous P34 Sequences of *Mycobacteria*

The P34 genes present in all *Mycobacteria* are all amplified with the following consensus primers:

Sense

MycU4 5' CATGCAGTGAATTAGAACGT 3' (SEQ ID NO: 53) located at the position 496–515 of the gene, Tm=56° C.

Antisense

APmcon02 5' GTASGTCATRRSTYCTCC 3' (SEQ ID NO: 54) located at the position position 733–750 of the gene, Tm=52–58° C.

S=C or G

R=A or G

Y=T or C

The size of amplified products ranges from 123 to 258 bp.

The following capture probes have been chosen for the specific capture of the *Mycobacteria* sequences:

Capture Probes:

Avium: (SEQ ID NO: 55)
5' CGGTCGTCTCCGAAGCCCGCG 3' (21 nt)

Gastrii 1: (SEQ ID NO: 56)
5' GATCGGCAGCGGTGCCGGGG 3' (20 nt)

Gastrii 3: (SEQ ID NO: 57)
5' GTATCGCGGGCGGCAAGGT 3' (19 nt)

Gastrii 5: (SEQ ID NO: 58)
5' TCTGCCGATCGGCAGCGGTGCCGG 3' (24 nt)

Gastrii 7: (SEQ ID NO: 59)
5' GCCGGGGCCGGTATTCGCGGGCGG 3' (24 nt)

Gordonae: (SEQ ID NO: 60)
5' GACGGGCACTAGTTGTCAGAGG 3' (22 nt)

Intracellulare 1: (SEQ ID NO: 61)
5' GGGCCGCCGGGGGCCTCGCCG 3' (21 nt)

Intracellulare 3: (SEQ ID NO: 62)
5' GCCTCGCCGCCCAAGACAGTG 3' (21 nt)

Leprae: (SEQ ID NO: 63)
5' GATTTCGGCGTCCATCGGTGGT 3' (22 nt)

Kansasi 1: (SEQ ID NO: 64)
5' GATCGTCGGCAGTGGTGACGG 3' (21 nt)

Kansasi 3: (SEQ ID NO: 65)
5' TCGTCGGCAGTGGTGAC 3' (17 nt)

Kansasi 5: (SEQ ID NO: 66)
5' ATCCGCCGATCGTCGGCAGTGGTGACG 3' (27 nt)

Malmoense: (SEQ ID NO: 67)
5' GACCCACAACACTGGTCGGCG 3' (21 nt)

Marinum: (SEQ ID NO: 68)
5' CGGAGGTGATGGCGCTGGTCG 3' (21 nt)

Scrofulaceum: (SEQ ID NO: 69)
5' CGGCGGCACGGATCGGCGTC 3' (20 nt)

Simiae: (SEQ ID NO: 70)
5' ATCGCTCCTGGTCGCGCCTA 3' (20 nt)

Szulgai: (SEQ ID NO: 71)
5' CCCGGCGCGACCAGCAGAACG 3' (21 nt)

Tuberculosis: (SEQ ID NO: 72)
5' GCCGTCCAGTCGTTAATGTCGC 3' (22 nt)

Xenopi: (SEQ ID NO: 73)
5' CGGTAGAAGCTGCGATGACACG 3' (22 nt)

Each of the sequences above comprises a spacer at its 5' end. Spacer sequence 5' GAATTCAAAGTTGCTGAGAAT-AGTTCAATGGAAGGAAGCG 3' (SEQ ID NO: 36). Capture probes are aminated at their 5' end.

Example 9

Detection of MAGE Genes

MAGE genes are all amplified with the following consensus primers

Sense

DPSCONS2 5' GGGCTCCAGCAGCCAAGAAGAGGA 3' (SEQ ID NO: 74), located at the 398–421 position of the gene. Tm=78° C.

Other amplicons have been added as sense primer in order to increase the efficiency of the PCR for some MAGEs (SEQ ID NO: 75)
DPSMAGE1 5' GGGTTCCAGCAGCCGTGAAGAGGA 3' Tm = 78° C.

(SEQ ID NO: 76)
DPSMAG8 5' GGGTTCCAGCAGCAATGAAGAGGA 3' Tm = 74° C.

(SEQ ID NO: 77)
DPSMAG12 5' GGGCTCCAGCAACGAAGAACAGGA 3' Tm = 76° C.

Antisense

DPASCONB4 5' CGGTACTCCAGGTAGTTTTCCTGC 3' (SEQ ID NO: 78), located at the position 913–936 of the gene, Tm=74° C.

The size of the amplified products is around 530 bp

The following capture probes of 27 nucleotides have been chosen for the specific capture of the MAGE sequences.

Capture Probe (SEQ ID NO: 79)
Mage 1 DTAS01   5' ACAAGGACTCCAGGATACAAGAGGTGC 3'

(SEQ ID NO: 80)
Mage 2 DTAS02   5' ACTCGGACTCCAGGTCGGGAAACATTC 3'

(SEQ ID NO: 81)
Mage 3 DTS0306  5' AAGACAGTATCTTGGGGGATCCCAAGA 3'

(SEQ ID NO: 82)
Mage 4 DTAS04   5' TCGGAACAAGGACTCTGCGTCAGGCGA 3'

(SEQ ID NO: 83)
Mage 5 DTAS05   5' GCTCGGAACACAGACTCTGGGTCAGGG 3'

(SEQ ID NO: 84)
Mage 6 DTS06    5' CAAGACAGGCTTCCTGATAATCATCCT 3'

(SEQ ID NO: 85)
Mage 7 DTAS07   5' AGGACGCCAGGTGAGCGGGGTGTGTCT 3'

(SEQ ID NO: 86)
Mage 8 DTAS08   5' GGGACTCCAGGTGAGCTGGGTCCGGGG 3'

(SEQ ID NO: 87)
Mage 9 DTAS09   5' TGAACTCCAGCTGAGCTGGGTCGACCG 3'

(SEQ ID NO: 88)
Mage 10 DTAS10  5' TGGGTAAAGACTCACTGTCTGGCAGGA 3'

(SEQ ID NO: 89)
Mage 11 DTAS11  5' GAAAAGGACTCAGGGTCTATCAGGTCA 3'

(SEQ ID NO: 90)
Mage 12 DTAS12  5' GTGCTACTTGGAAGCTCGTCTCCAGGT 3'

Each of the sequences above comprises a spacer aminated at its 5' end in order to be convalently linked to the glass.

Spacer sequence 5'GAATTCAAGTTGCTGAGAATAGT-TCAATGGAAGGAAGCG 3' (SEQ ID NO: 36)

They are spotted on aldehyde bearing glasses and used for the detection of the MAGEs amplified by the consensus primers given here above. The results show a non equivocal identification of the MAGEs present in the tumors compared to identification using 12 specific PCR, one for each MAGE sequences.

Example 10

Identification of G-Protein Dopamin Receptors Subtypes in Rat

Dopamine Receptor coupled to the G-protein are all amplified with the following consensus primers Sense

CONSENSUS2-3-4

5' TGCAGACMACCACCAACTACTT 3' (SEQ ID NO: 91) located at the position 221–242 of the gene, Tm=66° C.

M=A or C

CONSENSUS1-5

5' TGMGGKCCAAGATGACCAACWT 3' (SEQ ID NO: 92) (22 nt) located at the position 221–240 of the gene, Tm=66° C.

M=A or C

K=G or T

W=A or T

Antisense

5' TCATGRCRCASAGGTTCAGGAT 3' (SEQ ID NO: 93) located at the position 395–416 of the gene, Tm=64–68° C.

R=A or G

S=C or G

The size of the amplified product is 196 pb.

The following capture probes of 27 nucleotides have been chosen for the of the dopamine receptor sequences.

Capture Probes

```
                                          (SEQ ID NO: 94)
DRD1    5' CTGGCTTTTGGCCTTTGGGTCCCTTTT 3'

(SEQ ID NO: 95)
DRD2    5' TGATTGGAAATTCAGCAGGATTCACTG 3'

(SEQ ID NO: 96)
DRD3    5' GAGTCTGGAATTTCAGCCGCATTTGCT 3'

(SEQ ID NO: 97)
DRD4    5' CGTCTGGCTGCTGAGCCCCCGCCTCTG 3'

(SEQ ID NO: 98)
DRD5    5' CTGGGTACTGGCCCTTTGGGACATTCT 3'
```

Each of the sequences above comprises an aminated spacer at its 5' end. Spacer sequence 5' GAATTCAAAGT-TGCTGAGAATAGTTCAATGGAAGGAAGCG (SEQ ID NO: 36)

Example 11

Identification of G-Protein Histamin Receptors Subtypes in Rat

Histamin Receptor coupled to the G-protein are all amplified with the following primers.

Sense

H1sense

5'CTCCGTCCAGCAACCCCT 3' (SEQ ID NO: 99) (18 nt) located at the Position 381–398 of the gene, Tm=60° C.

H2sense

5'CTGTGCTGGTCACCCCAGT 3' (SEQ ID NO: 100) (18 nt) located at the Position 380–398 of the gene, Tm=62° C.

H3sense

5' ACTCATCAGCTATGACCGATT (SEQ ID NO: 101) 3'(21 nt) located at the Position 378–398 of the gene, Tm=60° C.

Antisense

H1antisense

5' ACCTTCCTTGGTATCGTCTG 3' (SEQ ID NO: 102) (20 nt) located at the Position 722–741 of the gene, Tm=60° C.

H2antisense

5' GAAACCAGCAGATGATGAACG 3' (SEQ ID NO: 103) (21 nt) located at the Position 722–742 of the gene, Tm=62° C.

H3antisense

5' GCATCTGGTGGGGGTTCTG 3' (SEQ ID NO: 104) (19 nt) located at the Position 722–740 of the gene, Tm=62° C.

Size of the amplified product ranges from 359 to 364 bp.

The following capture probes have been chosen for the specific capture of the histamin receptor sequences.

Capture Probes

```
                                       (SEQ ID NO: 105)
H1    5' CCCCAGGATGGTAGCGGA 3' (18 nt)

(SEQ ID NO: 106)
H2    5' AGGATAGGGTGATAGAAATAAC 3' (22 nt)

(SEQ ID NO: 107)
H3    5' TCTCGTGTCCCCCTGCTG 3' (18 nt)
```

Each of the sequences above comprises a spacer at its 5' end. Spacer sequence 5' GAATTCAAAGTTGCTGAGAAT-AGTTCAATGGAAGGAAGCG 3' (SEQ ID NO: 36). Capture probes are aminated at their 5' end.

Example 12

Identification of G-Protein Serotonin Receptors Subtypes in Rat

Serotonin Receptor coupled to the G-protein are all amplified with the following primers Sense Consensus for the subtypes 1A, 1B, 1C, 1D, 1E, 2A, 2B, 2C, 4, 6, 7

5'ATCHTGCACCTSTGBGBCAT 3' (SEQ ID NO: 108) Tm=58–64° C. (20 nt)

H=C or A or T

S=C or G

B=C or T or G

1A
ATCCTGCACCTGTGCGCCAT (0 mismatch) position 370–389 (SEQ ID NO: 109)

1B
ATCATGCATCTCTGTGTCAT (1 mismatch) position 397–416 (SEQ ID NO: 110)

1C
ATCATGCACCTCTGCGCCAT (0 mismatch) position 427–446 (SEQ ID NO: 111)

1D
ATCCTGCATCTCTGTGTCAT (1 mismatch) position 367–386 (SEQ ID NO: 112)

1E
ATCTTGCACCTGTCGGCTAT (2 mismatch) position 331–350 (SEQ ID NO: 113)

2A
ATCATGCACCTCTGCGCCAT (0 mismatch) position 487–506 (SEQ ID NO: 114)

2B
ATCATGCATCTCTGTGCCAT (1 mismatch) position 424–443 (SEQ ID NO: 115)

2C
ATCATGCACCTCTGCGCCAT (0 mismatch) position 24–43 (SEQ ID NO: 116)

4
ATTTTTCACCTCTGCTGCAT (3 mismatchs) (SEQ ID NO: 117)

6
ATCCTCAACCTCTGCTTCAT (3 mismatchs) (SEQ ID NO: 118)

7
ATCATGACCCTGTGCGTGAT (3 mismatchs) (SEQ ID NO: 119)

Consensus 4, 6

5' ATCYTYCACCTCTGCYKCAT 3' (SEQ ID NO: 120)
Tm=52–64° C. (20 nt)

K=G or T

N=T or C

Y=T or C

4
ATTTTTCACCTCTGCTGCAT (1 mismatch) position 322–341 (SEQ ID NO: 121)

6
ATCCTCAACCTCTGCCTCAT (1 mismatch) position 340–359 (SEQ ID NO: 122)

Consensus 5A, 5B

5' ATCTGGAAYGTGRCAGCCAT 3' (SEQ ID NO: 123)
Tm=58–62° C. (20 nt)

N=T or C

R=A or G

5A
ATCTGGAATGTGACAGCAAT (1 mismatch) position 385–404 (SEQ ID NO: 124)

5B
ATCTGGAACGTGGCGGCCAT (1 mismatch) position 424–443 (SEQ ID NO: 125)

Specific 7

5' ATCATGACCCTGTGCGTGAT 3' (SEQ ID NO: 126)
Tm=56° C. (18 nt) position 517–536

Specific 3B

5' CTTCCGGAACGATTAGAAA 3' (SEQ ID NO: 127)
Tm=54° C. (19 nt) position 404–422

Antisense
Consensus for the subtypes 1A, 1B, 1C, 1D, 1E, 2A, 2B, 2C, 4, 7 Tm=48–58° C.

5' TTGGHNGCYTTCYGBTC 3' (SEQ ID NO: 128)

H=A or T or C

N=A or C or G or T

B=C or T or G

1A
TTCACCGTCTTCCTTTC (4 mismatchs) (SEQ ID NO: 129)

1B
TTGGTGGCTTTGCGCTC (1 mismatch) position 913–929 (SEQ ID NO: 130)

1C
TTGGAAGCTTTCTTTTC (1 mismatch) position 922–938 (SEQ ID NO: 131)

1D
TTAGTGGCTTTCCTTTC (2 mismatchs) position 877–893 (SEQ ID NO: 132)

1E
GTGGCTGCTTTGCGTTC (2 mismatchs) position 862–878 (SEQ ID NO: 133)

2A
TTGCACGCCTTTTGCTC (2 mismatchs) position 952–968 (SEQ ID NO: 134)

2B
TTTGAGGCTCTCTGTTC (2 mismatchs) position 952–968 (SEQ ID NO: 135)

2C
TTGGAAGCTTTCTTTTC (1 mismatch) position 424–440 (SEQ ID NO: 136)

4
TTGGCTGCTTTCCGGTC (2 mismatchs) (SEQ ID NO: 137)

7
GTGGCTGCTTTCTGTTC (1 mismatch) position 973–989 (SEQ ID NO: 138)

Specific 1A

5' TTCACCGTCTTCCTTTC 3' Tm=50° C. (17 nt) position 1018–1034 (SEQ ID NO: 139)

Specific 4

5' TCTTGGCTGCTTTGGTC 3' Tm=52° C. (17 nt) position 762–778 (SEQ ID NO: 140)

Specific 6

5' ATAAAGAGCGGGTAGATG 3' Tm=52° C. (18 nt) position 945–963 (SEQ ID NO: 141)

Consensus 5A, 5B

5'CCTTCTGCTCCCTCCA 3' (SEQ ID NO: 142) Tm=52° C. (16 nt)

```
                                              (SEQ ID NO: 143)
5A  CCTTCTGTTCCCTCCA (1 mismatch) position 823-840

(SEQ ID NO: 144)
5B  CCTTCTGCTCCCGCCA (1 mismatch) position 862-879
```

Specific 3B

5' ACCGGGGACTCTGTGT 3' (SEQ ID NO: 145) Tm=52° C. (16 nt) position 1072–1089

The following capture probes have been chosen for the specific capture of the serotonin receptor subtypes sequences.

Capture Probes

```
                                              (SEQ ID NO: 146)
HTR1C      5' CTATGCTCAATAGGATTACGT 3' (21 nt)

(SEQ ID NO: 147)
HTR2A      5' GTGGTGAATGGGGTTCTGG 3' (19 nt)

(SEQ ID NO: 148)
HTR2B      5' TGGCCTGAATTGGCTTTTTGA 3' (21 nt)

(SEQ ID NO: 149)
HTR2C/1C   5' TTATTCACGAACACTTTGCTTT 3' (22 nt)

(SEQ ID NO: 150)
HTR1B      5' AATAGTCCACCGCATCAGTG 3' (20 nt)

(SEQ ID NO: 151)
HTR1D      5' GTACTCCAGGGCATCGGTG 3' (19 nt)

(SEQ ID NO: 152)
HTR1A      5' CATAGTCTATAGGGTCGGTG 3' (20 nt)

(SEQ ID NO: 153)
HTR1E      5' ATACTCGACTGCGTCTGTGA 3' (20 nt)

(SEQ ID NO: 154)
HTR7       5' GTACGTGAGGGGTCTCGTG 3' (19 nt)

(SEQ ID NO: 155)
HTR5A      5' GGCGCGTTATTGACCAGTA 3' (19 nt)

(SEQ ID NO: 156)
HTR5B      5' GGCGCGTGATAGTCCAGT 3' (18 nt)

(SEQ ID NO: 157)
HTR3B      5' GATATCAAAGGGGAAAGCGTA 3' (21 nt)

(SEQ ID NO: 158)
HTR4       5' AAACCAAAGGTTGACAGCAG 3' (20 nt)

(SEQ ID NO: 159)
HTR6       5' GTAGCGCAGCGGCGAGAG 3' (18 nt)
```

Each of the sequences above comprises a spacer at its 5' end. Spacer sequence 5' GAATTCAAAGTTGCTGAGAATAGTTCAATGGAAGGAAGCG 3' (SEQ ID NO: 36). Capture probes are aminated at their 5' end.

Example 13

Identification of the HLA-A Subtypes

The HLA-A subtypes are amplified with the following consensus primers

Sense

IPSCONA 5' GACAGCGACGCCGCGAGCCA 3' (SEQ ID NO: 160) located at the position 181–200 of the gene, Tm=70° C.

Antisense

IPASCONA 5' CGTGTCCTGGGTCTGGTCCTCC 3' (SEQ ID NO: 161) located at the position 735–754 of the gene, Tm=74° C.

The size of the amplified product is 574 bp

The following capture probes of 27 nucleotides have been chosen for the specific capture of the HLA-A sequences Capture Probes

```
                                              (SEQ ID NO: 162)
HLA-A1   ITSA01   5' GGAGGGCCGGTGCGTGGACGGGCTCCG 3'

(SEQ ID NO: 163)
HLA-A2   ITASA02  5' TCTCCCCGTCCCAATACTCCGGACCCT 3'

(SEQ ID NO: 164)
HLA-A3   ITASA03A 5' CTGGGCCTTCACATTCCGTGTCTCCTG 3'

(SEQ ID NO: 165)
         ITSA03B  5' AGCGCAAGTGGGAGGCGGCCCATGAGG 3'

(SEQ ID NO: 166)
HLA-A11  ITSA11A  5' GCCCATGCGGCGGAGCAGCAGAGAGCC 3'

(SEQ ID NO: 167)
         ITSA11B  5' CCTGGAGGGCCGGTGCGTGGAGTGGCT 3'

(SEQ ID NO: 168)
HLA-A23  ITSA23A  5' GCCCGTGTGGCGGAGCAGTTGAGAGCC 3'

(SEQ ID NO: 169)
         ITASA23B 5' CCTTCACTTTCCCTGTCTCCTCGTCCC 3'

(SEQ ID NO: 170)
HLA-A24  ITSA24A  5' GCCCATGTGGCGGAGCAGCAGAGAGCC 3'

(SEQ ID NO: 171)
         ITASA24B 5' TAGCGGAGCGCGATCCGCAGGTTCTCT 3'

(SEQ ID NO: 172)
HLA-A25  ITASA25A 5' TAGCGGAGCGCGATCCGCAGGCTCTCT 3'

(SEQ ID NO: 173)
         ITASA25B 5' TCACATTCCGTGTGTTCCGGTCCCAAT 3'

(SEQ ID NO: 174)
HLA-A26  ITASA26  5' GGGTCCCCAGGTTCGCTCGGTCAGTCT 3'

(SEQ ID NO: 175)
HLA-A29  ITASA29  5' TCACATTCCGTGTCTGCAGGTCCCAAT 3'

(SEQ ID NO: 176)
HLA-A30  ITASA30  5' CGTAGGCGTGCTGTTCATACCCGCGGA 3'

(SEQ ID NO: 177)
HLA-A31  ITASA31  5' CCCAATACTCAGGCCTCTCCTGCICTA 3'

(SEQ ID NO: 178)
HLA-A33  ITSA33   5' CGCACGGACCCCCCCAGGACGCATATG 3'

(SEQ ID NO: 179)
HLA-A68  ITSA68A  5' GGCGGCCCATGTGGCGGAGCAGTGGAG 3'
```

-continued

ITASA68B 5' GTCGTAGGCGTCCTGCCGGTACCCGCG 3' (SEQ ID NO: 180)

HLA-A69 ITASA69 5' ATCCTCTGGACGGTGTGAGAACCGGCC 3' (SEQ ID NO: 181)

Each of the sequences above comprises an aminated spacer at its 5' end. Spacer sequence 5' GAATTCAAAGT-TGCTGAGAATAGTTCAATGGAAGGAAGCG 3' (SEQ ID NO: 36).

Example 14

Identification of Cytochrome P450 3a Forms

The Cytochrome P450 forms are amplified with the following consensus primers

Sense
 Consensus

5' GCCAGAGCCTGAGGA 3' (SEQ ID NO: 182) located at the position 1297–1311 of the 3a3 gene, Tm=50° C.

Antisense
 Consensus a3, a23, a1, a2

5' TCAAAAGAAATTAACAGAGA 3' (SEQ ID NO: 183) located at the position 1839–1858 of the 3a3 gene, Tm=50° C.

Specific a9

5' ACAATGAAGGTAACATAGG 3' (SEQ ID NO: 184) located at the position 2015–2033 of the 3a9 gene Tm=52° C.

Specific a18

5' ACTGATGGAACTAACTGG 3' (SEQ ID NO: 185) located at the position 1830–1846 of the 3a18 gene Tm=52° C.

The length of the PCR product is around 560 bp.

The following capture probes have been chosen for the specific capture of the cytochrome P-450 3a sequences.

Capture Probe

3a1   5' TGTTTTGATTCGGTACATCTTTG 3' (23 nt) (SEQ ID NO: 186)

3a3   5' TTGATTTGGTACATCTTTGCT 3' (21 nt) (SEQ ID NO: 187)

3A9   5' ACTCCTGGGGTTTTGGGTG 3' (20 nt) (SEQ ID NO: 188)

3A18  5' ATTACTGAGTATTCAGAAATTCAC 3' (24 nt) (SEQ ID NO: 189)

3A2   5' GGTTAAAGATTTGGTACATTTATGG 3' (25 nt) (SEQ ID NO: 190)

Each of the sequences above comprises a spacer at its 5' end. Spacer sequence 5' GAATTCAAAGTTGCTGAGAAT-AGTTCAATGGAAGGAAGCG 3' (SEQ ID NO: 36). Capture probes are aminated at their 5' end.

Example 15

Identification of GMO on Biochips

Consensus primers to detect GMO on biochips:

OGM1   CGTCTTCAAAGCAAGTGGATTG (SEQ ID NO: 191)

OGM2   ATCCTGTTGCCGGTCTTGCG (SEQ ID NO: 192)

These primers allow the amplification of the genes:

1) CTP1, CTP2, CP4EPSPS, S CryIAb and hsp 70 Int. in Mon 809 (corn, Monsanto)

2) hsp 70 Int. and S CryIAb in Mon 810 (corn, Monsanto)

3) S CryIAb and S Pat in Bt 11 (corn, Novartis)

4) CTP4 and EPSPS in GTS40-3-2 (soybean, Monsanto)

The capture probes will be chosen in these sequences to allow discrimination. Each of the sequences above comprises a spacer at its 5' end. Spacer sequence 5' GAAT-TCAAAGTTGCTGAGAATAGTTCAATG-GAAGGAAGCG (SEQ ID NO: 36).

What is claimed is:

1. A method for identifying and/or quantifying an organism or part of an organism in a sample by detecting a nucleotide sequence specific of said organism, wherein said specific nucleotide sequence presents a homology higher than 30% with at least 4 other homologous nucleotide sequences from other organisms comprising:

amplifying said specific nucleotide sequence by PCR into double-stranded target nucleotide sequence using primer pairs which are capable of amplifying at least two of said homologous nucleotide sequences from other organisms so as to produce a full-length target nucleotide sequence having between 100 and 800 bases;

contacting said target nucleotide sequence resulting from the amplifying step with single-stranded capture nucleotide sequences, said single-stranded capture nucleotide sequences being covalently bound in an array to an insoluble solid support via a spacer comprising a nucleotide sequence of at least 40 bases in length, wherein said array comprises at least 4 different bound single-stranded capture nucleotide sequences/cm$^2$ of solid support surface and wherein said capture nucleotide sequences comprise a nucleotide sequence of about 15 to about 40 bases which is able to specifically bind to said full-length target nucleotide sequence without binding to said at least 4 homologous nucleotide sequences; and detecting specific hybridization of said target nucleotide sequence to said capture nucleotide sequences.

2. The method according to claim 1, wherein the amplified nucleotide sequence is a DNA nucleotide sequence.

3. The method according to claim 1, wherein the amplified nucleotide sequences are mRNA first reverse transcribed into cDNA and then amplified using said primer pair which is capable of amplifying at least two of said homologous mRNA in said sample.

4. The method according to claim 1, wherein the density of the capture nucleotide sequence bound to the surface at a specific location is more than about 10 fmoles per cm$^2$ of solid support surface.

5. The method according to claim 1, wherein the target nucleotide sequence presents a homology with other homologous nucleotide sequences higher than 60%.

6. The method according to claim 1, wherein other primers are present in the amplification step for the amplification of another nucleotide sequence.

7. The method according to claim 1, wherein the insoluble solid support is selected from the group consisting of: glasses, electronic devices, silicon supports, plastic supports, compact discs, filters, gel layers, and metallic supports.

8. The method according to claim 1, wherein the nucleotide sequence to be identified and/or quantified is an RNA sequence submitted to a reverse transcription of its 3' or 5' end by using a consensus primer.

9. The method according to claim 1, wherein the nucleotide sequence to be identified and/or quantified are from the FemA gene of *Staphylococci* species selected from the group consisting of: *S. aureus, S. epidermidis, S. saprophyticus, S. hominis* and *S. haemolyticus*.

10. The method according to claim 1, wherein the solid support also bears capture nucleotide sequences specific of the homologous sequences specific for the binding with the homologous target nucleotide sequence together with a consensus sequence able to bind to said target nucleotide sequence and to said at least 4 homologous nucleotide sequences.

11. The method according to claim 1, wherein the solid support bears capture nucleotide sequences specific for the identification of two or more *staphylococcus* species together with a consensus sequence for a *Staphylococcus* genus identification.

12. The method according to claim 1, wherein the sequence to be identified and/or quantified in the sample belongs to the MAGE gene family.

13. The method according to claim 1, wherein the sequence to be identified and/or quantified in the sample belongs to the HLA-A genes family.

14. The method according to claim 1, wherein the sequence to be identified and/or quantified in the sample belongs to the dopamine receptors coupled to the protein G genes family.

15. The method according to claim 1, wherein the sequence to be identified and/or quantified in the sample belongs to the choline receptors coupled to the protein G genes family.

16. The method according to claim 1, wherein the sequence to be detected and/or quantified in the sample belongs to the histamine receptors coupled to the protein G genes family.

17. The method according to claim 1, wherein the sequence to be detected and/or quantified in the sample belongs to the cytochrome p450 forms family.

18. The method of claim 1, wherein said nucleotide sequence to be identified and/or quantified originates from a microorganism.

19. The method according to claim 1, wherein the density of the capture nucleotide sequence bound to the surface at a specific location is more than about 100 fmoles per $cm^2$ of solid support surface.

20. The method according to claim 1, wherein the target nucleotide sequence presents a homology with other homologous nucleotide sequences higher than 80%.

21. The method of claim 6, wherein said other nucleotide sequence is an antibiotic resistance determining sequence.

22. The method of claim 1, wherein said organism is identified or quantitated by detecting a single spot signal at one specific location on said insoluble solid support.

* * * * *

SEQUENCE LISTING

```
<160> NUMBER OF SEQ ID NOS: 192

<210> SEQ ID NO 1
<211> LENGTH: 23
<212> TYPE: DNA
<213> ORGANISM: Artificial Sequence
<220> FEATURE:
<223> OTHER INFORMATION: primer for amplification of S. aureus

<400> SEQUENCE: 1
cttttgctga tcgtgatgac aaa                                            23

<210> SEQ ID NO 2
<211> LENGTH: 25
<212> TYPE: DNA
<213> ORGANISM: Artificial Sequence
<220> FEATURE:
<223> OTHER INFORMATION: primer for amplification of S. aureus

<400> SEQUENCE: 2
```

```
tttatttaaa atatcacgct cttcg                                          25

<210> SEQ ID NO 3
<211> LENGTH: 23
<212> TYPE: DNA
<213> ORGANISM: Artificial Sequence
<220> FEATURE:
<223> OTHER INFORMATION: primer for amplification of S. epidermidis

<400> SEQUENCE: 3
tcgcggtcca gtaatagatt ata                                            23

<210> SEQ ID NO 4
<211> LENGTH: 22
<212> TYPE: DNA
<213> ORGANISM: Artificial Sequence
<220> FEATURE:
<223> OTHER INFORMATION: primer for amplification of S. epidermidis

<400> SEQUENCE: 4
tgcatttcca gttatttctc cc                                             22

<210> SEQ ID NO 5
<211> LENGTH: 24
<212> TYPE: DNA
<213> ORGANISM: Artificial Sequence
<220> FEATURE:
<223> OTHER INFORMATION: primer for amplification of S. haemolyticus

<400> SEQUENCE: 5
attgatcatg gtattgatag atac                                           24

<210> SEQ ID NO 6
<211> LENGTH: 25
<212> TYPE: DNA
<213> ORGANISM: Artificial Sequence
<220> FEATURE:
<223> OTHER INFORMATION: primer for amplification of S. haemolyticus

<400> SEQUENCE: 6
tttaatcttt tgagtgtct tatac                                           25

<210> SEQ ID NO 7
<211> LENGTH: 25
<212> TYPE: DNA
<213> ORGANISM: Artificial Sequence
<220> FEATURE:
<223> OTHER INFORMATION: primer for amplification of S. saprophyticus

<400> SEQUENCE: 7
taaaatgaaa caactcggtt ataag                                          25

<210> SEQ ID NO 8
<211> LENGTH: 24
<212> TYPE: DNA
<213> ORGANISM: Artificial Sequence
<220> FEATURE:
<223> OTHER INFORMATION: primer for amplification of S. saprophyticus

<400> SEQUENCE: 8
aaactatcca taccattaag tacg                                           24

<210> SEQ ID NO 9
<211> LENGTH: 24
<212> TYPE: DNA
```

```
-continued
<213> ORGANISM: Artificial Sequence
<220> FEATURE:
<223> OTHER INFORMATION: primer for amplification of S. hominis

<400> SEQUENCE: 9
cgaccagata acaaaaaagc acaa                                          24

<210> SEQ ID NO 10
<211> LENGTH: 22
<212> TYPE: DNA
<213> ORGANISM: Artificial Sequence
<220> FEATURE:
<223> OTHER INFORMATION: primer for amplification of S. hominis

<400> SEQUENCE: 10
gtaattcgtt accatgttct aa                                            22

<210> SEQ ID NO 11
<211> LENGTH: 27
<212> TYPE: DNA
<213> ORGANISM: Artificial Sequence
<220> FEATURE:
<223> OTHER INFORMATION: capture nucleotide ATaur02

<400> SEQUENCE: 11
atttaaaata tcacgctctt cgtttag                                       27

<210> SEQ ID NO 12
<211> LENGTH: 27
<212> TYPE: DNA
<213> ORGANISM: Artificial Sequence
<220> FEATURE:
<223> OTHER INFORMATION: capture nucleotide ATepi02

<400> SEQUENCE: 12
attaagcaca tttctttcat tatttag                                       27

<210> SEQ ID NO 13
<211> LENGTH: 27
<212> TYPE: DNA
<213> ORGANISM: Artificial Sequence
<220> FEATURE:
<223> OTHER INFORMATION: capture nucleotide AThae02

<400> SEQUENCE: 13
atttaaagtt tcacgttcat tttgtaa                                       27

<210> SEQ ID NO 14
<211> LENGTH: 27
<212> TYPE: DNA
<213> ORGANISM: Artificial Sequence
<220> FEATURE:
<223> OTHER INFORMATION: capture nucleotide AThom02

<400> SEQUENCE: 14
atttaatgtc tgacgttctg catgaag                                       27

<210> SEQ ID NO 15
<211> LENGTH: 27
<212> TYPE: DNA
<213> ORGANISM: Artificial Sequence
<220> FEATURE:
<223> OTHER INFORMATION: capture nucleotide ATsap02

<400> SEQUENCE: 15
acttaatact tcgcgttcag cctttaa                                       27
```

-continued

```
<210> SEQ ID NO 16
<211> LENGTH: 24
<212> TYPE: DNA
<213> ORGANISM: Artificial Sequence
<220> FEATURE:
<223> OTHER INFORMATION: consensus primer APstap03

<400> SEQUENCE: 16
cccactcgct tatatagaat ttga                                          24

<210> SEQ ID NO 17
<211> LENGTH: 23
<212> TYPE: DNA
<213> ORGANISM: Artificial Sequence
<220> FEATURE:
<223> OTHER INFORMATION: consensus primer APstap04

<400> SEQUENCE: 17
ccactagcgt acatcaattt tga                                           23

<210> SEQ ID NO 18
<211> LENGTH: 25
<212> TYPE: DNA
<213> ORGANISM: Artificial Sequence
<220> FEATURE:
<223> OTHER INFORMATION: consensus primer APstap05

<400> SEQUENCE: 18
ggtttaataa agtcaccaac atatt                                         25

<210> SEQ ID NO 19
<211> LENGTH: 47
<212> TYPE: DNA
<213> ORGANISM: Artificial Sequence
<220> FEATURE:
<223> OTHER INFORMATION: capture nucleotide (with spacer sequence)
      ATepi03
<221> NAME/KEY: misc_feature
<222> LOCATION: (1)...(20)
<223> OTHER INFORMATION: spacer sequence

<400> SEQUENCE: 19
gaattcaaag ttgctgagaa attaagcaca tttctttcat tatttag                 47

<210> SEQ ID NO 20
<211> LENGTH: 67
<212> TYPE: DNA
<213> ORGANISM: Artificial Sequence
<220> FEATURE:
<223> OTHER INFORMATION: capture nucleotide (with spacer sequence)
      ATepi04
<221> NAME/KEY: misc_feature
<222> LOCATION: (1)...(40)
<223> OTHER INFORMATION: spacer sequence

<400> SEQUENCE: 20
gaattcaaag ttgctgagaa tagttcaatg gaaggaagcg attaagcaca tttctttcat   60
tatttag                                                             67

<210> SEQ ID NO 21
<211> LENGTH: 87
<212> TYPE: DNA
<213> ORGANISM: Artificial Sequence
<220> FEATURE:
<223> OTHER INFORMATION: capture nucleotide (with spacer sequence)
      ATepi05
```

```
<221> NAME/KEY: misc_feature
<222> LOCATION: (1)...(60)
<223> OTHER INFORMATION: spacer sequence

<400> SEQUENCE: 21
gaattcaaag ttgctgagaa tagttcaatg gaaggaagcg tcttcttaaa atctaaagaa    60
attaagcaca tttctttcat tatttag                                       87

<210> SEQ ID NO 22
<211> LENGTH: 67
<212> TYPE: DNA
<213> ORGANISM: Artificial Sequence
<220> FEATURE:
<223> OTHER INFORMATION: capture nucleotide (with spacer sequence)
      Ataur27
<221> NAME/KEY: misc_feature
<222> LOCATION: (1)...(40)
<223> OTHER INFORMATION: spacer sequence

<400> SEQUENCE: 22
gaattcaaag ttgctgagaa tagttcaatg gaaggaagcg atttaaaata tcacgctctt    60
cgtttag                                                             67

<210> SEQ ID NO 23
<211> LENGTH: 67
<212> TYPE: DNA
<213> ORGANISM: Artificial Sequence
<220> FEATURE:
<223> OTHER INFORMATION: capture nucleotide (with spacer sequence)
      Atepi27
<221> NAME/KEY: misc_feature
<222> LOCATION: (1)...(40)
<223> OTHER INFORMATION: spacer sequence

<400> SEQUENCE: 23
gaattcaaag ttgctgagaa tagttcaatg gaaggaagcg attaagcaca tttctttcat    60
tatttag                                                             67

<210> SEQ ID NO 24
<211> LENGTH: 67
<212> TYPE: DNA
<213> ORGANISM: Artificial Sequence
<220> FEATURE:
<223> OTHER INFORMATION: capture nucleotide (with spacer sequence)
      Athae27
<221> NAME/KEY: misc_feature
<222> LOCATION: (1)...(40)
<223> OTHER INFORMATION: spacer sequence

<400> SEQUENCE: 24
gaattcaaag ttgctgagaa tagttcaatg gaaggaagcg atttaaagtt tcacgttcat    60
tttgtaa                                                             67

<210> SEQ ID NO 25
<211> LENGTH: 67
<212> TYPE: DNA
<213> ORGANISM: Artificial Sequence
<220> FEATURE:
<223> OTHER INFORMATION: capture nucleotide (with spacer sequence)
      Athom27
<221> NAME/KEY: misc_feature
<222> LOCATION: (1)...(40)
<223> OTHER INFORMATION: spacer sequence

<400> SEQUENCE: 25
gaattcaaag ttgctgagaa tagttcaatg gaaggaagcg atttaatgtc tgacgttctg    60
``` catgaag 67

<210> SEQ ID NO 26
<211> LENGTH: 67
<212> TYPE: DNA
<213> ORGANISM: Artificial Sequence
<220> FEATURE:
<223> OTHER INFORMATION: capture nucleotide (with spacer sequence)
      Atsap27
<221> NAME/KEY: misc_feature
<222> LOCATION: (1)...(40)
<223> OTHER INFORMATION: spacer sequence

<400> SEQUENCE: 26
gaattcaaag ttgctgagaa tagttcaatg gaaggaagcg acttaatact tcgcgttcag    60
cctttaa    67

<210> SEQ ID NO 27
<211> LENGTH: 22
<212> TYPE: DNA
<213> ORGANISM: Artificial Sequence
<220> FEATURE:
<223> OTHER INFORMATION: consensus primer APcons3-1

<400> SEQUENCE: 27
taayaaartc accaacatay tc    22

<210> SEQ ID NO 28
<211> LENGTH: 22
<212> TYPE: DNA
<213> ORGANISM: Artificial Sequence
<220> FEATURE:
<223> OTHER INFORMATION: consensus primer APcons3-2
<221> NAME/KEY: misc_feature
<222> LOCATION: (1)...(22)
<223> OTHER INFORMATION: n = A,T,C or G

<400> SEQUENCE: 28
tymgntcatt tatggaagat ac    22

<210> SEQ ID NO 29
<211> LENGTH: 67
<212> TYPE: DNA
<213> ORGANISM: Artificial Sequence
<220> FEATURE:
<223> OTHER INFORMATION: capture nucleotide (with spacer sequence)
      Ataur15
<221> NAME/KEY: misc_feature
<222> LOCATION: (1)...(52)
<223> OTHER INFORMATION: spacer sequence

<400> SEQUENCE: 29
gaattcaaag ttgctgagaa tagttcaatg gaaggaagcg tcttcttaaa atgctcttcg    60
tttagtt    67

<210> SEQ ID NO 30
<211> LENGTH: 67
<212> TYPE: DNA
<213> ORGANISM: Artificial Sequence
<220> FEATURE:
<223> OTHER INFORMATION: capture nucleotide (with spacer sequence)
      Ataur40
<221> NAME/KEY: misc_feature
<222> LOCATION: (1)...(27)
<223> OTHER INFORMATION: spacer sequence

<400> SEQUENCE: 30

```
gaattcaaag ttgctgagaa tagttcaaat ctttatttaa aatatcacgc tcttcgttta      60
gttcttt                                                                67

<210> SEQ ID NO 31
<211> LENGTH: 67
<212> TYPE: DNA
<213> ORGANISM: Artificial Sequence
<220> FEATURE:
<223> OTHER INFORMATION: capture nucleotide (with spacer sequence)
      Atana15
<221> NAME/KEY: misc_feature
<222> LOCATION: (1)...(52)
<223> OTHER INFORMATION: spacer sequence

<400> SEQUENCE: 31
gaattcaaag ttgctgagaa tagttcaatg gaaggaagcg tcttcttaaa atgctcttca      60
tttagtt                                                                67

<210> SEQ ID NO 32
<211> LENGTH: 67
<212> TYPE: DNA
<213> ORGANISM: Artificial Sequence
<220> FEATURE:
<223> OTHER INFORMATION: capture nucleotide (with spacer sequence)
      Atana27
<221> NAME/KEY: misc_feature
<222> LOCATION: (1)...(40)
<223> OTHER INFORMATION: spacer sequence

<400> SEQUENCE: 32
gaattcaaag ttgctgagaa tagttcaatg gaaggaagcg gtttaaaata tcacgctctt      60
catttag                                                                67

<210> SEQ ID NO 33
<211> LENGTH: 67
<212> TYPE: DNA
<213> ORGANISM: Artificial Sequence
<220> FEATURE:
<223> OTHER INFORMATION: capture nucleotide (with spacer sequence)
      Atana40
<221> NAME/KEY: misc_feature
<222> LOCATION: (1)...(27)
<223> OTHER INFORMATION: spacer sequence

<400> SEQUENCE: 33
gaattcaaag ttgctgagaa tagttcaaat ctttgtttaa aatatcacgc tcttcattta      60
gttcttt                                                                67

<210> SEQ ID NO 34
<211> LENGTH: 67
<212> TYPE: DNA
<213> ORGANISM: Artificial Sequence
<220> FEATURE:
<223> OTHER INFORMATION: capture nucleotide (with spacer sequence)
      Atepi15
<221> NAME/KEY: misc_feature
<222> LOCATION: (1)...(52)
<223> OTHER INFORMATION: spacer sequence

<400> SEQUENCE: 34
gaattcaaag ttgctgagaa tagttcaatg gaaggaagcg tcttcttaaa attttcatta      60
tttagtt                                                                67

<210> SEQ ID NO 35
```

```
<211> LENGTH: 67
<212> TYPE: DNA
<213> ORGANISM: Artificial Sequence
<220> FEATURE:
<223> OTHER INFORMATION: capture nucleotide (with spacer sequence)
      Atepi40
<221> NAME/KEY: misc_feature
<222> LOCATION: (1)...(27)
<223> OTHER INFORMATION: spacer sequence

<400> SEQUENCE: 35
gaattcaaag ttgctgagaa tagttcaaat ctttattaag cacatttctt tcattattta      60
gttcctc                                                                67

<210> SEQ ID NO 36
<211> LENGTH: 40
<212> TYPE: DNA
<213> ORGANISM: Artificial Sequence
<220> FEATURE:
<223> OTHER INFORMATION: spacer sequence

<400> SEQUENCE: 36
gaattcaaag ttgctgagaa tagttcaatg gaaggaagcg                            40

<210> SEQ ID NO 37
<211> LENGTH: 27
<212> TYPE: DNA
<213> ORGANISM: Artificial Sequence
<220> FEATURE:
<223> OTHER INFORMATION: S. aureus femA capture sequence

<400> SEQUENCE: 37
atttaaaata tcacgctctt cgtttag                                          27

<210> SEQ ID NO 38
<211> LENGTH: 27
<212> TYPE: DNA
<213> ORGANISM: Artificial Sequence
<220> FEATURE:
<223> OTHER INFORMATION: S. epidermidis femA capture sequence

<400> SEQUENCE: 38
attaagcaca tttctttcat tatttag                                          27

<210> SEQ ID NO 39
<211> LENGTH: 27
<212> TYPE: DNA
<213> ORGANISM: Artificial Sequence
<220> FEATURE:
<223> OTHER INFORMATION: S. haemolyticus femA capture sequence

<400> SEQUENCE: 39
atttaaagtt tcacgttcat tttgtaa                                          27

<210> SEQ ID NO 40
<211> LENGTH: 27
<212> TYPE: DNA
<213> ORGANISM: Artificial Sequence
<220> FEATURE:
<223> OTHER INFORMATION: S. hominis femA capture sequence

<400> SEQUENCE: 40
atttaatgtc tgacgttctg catgaag                                          27

<210> SEQ ID NO 41
<211> LENGTH: 27
```

```
<212> TYPE: DNA
<213> ORGANISM: Artificial Sequence
<220> FEATURE:
<223> OTHER INFORMATION: S. saprophyticus femA capture sequence

<400> SEQUENCE: 41
acttaatact tcgcgttcag cctttaa                                              27

<210> SEQ ID NO 42
<211> LENGTH: 27
<212> TYPE: DNA
<213> ORGANISM: Artificial Sequence
<220> FEATURE:
<223> OTHER INFORMATION: S. capitis femA capture sequence

<400> SEQUENCE: 42
attaagaaca tctctttcat tattaag                                              27

<210> SEQ ID NO 43
<211> LENGTH: 24
<212> TYPE: DNA
<213> ORGANISM: Artificial Sequence
<220> FEATURE:
<223> OTHER INFORMATION: S. caseolyticus femA capture sequence

<400> SEQUENCE: 43
ataaagacat tcgagacgaa ggct                                                 24

<210> SEQ ID NO 44
<211> LENGTH: 27
<212> TYPE: DNA
<213> ORGANISM: Artificial Sequence
<220> FEATURE:
<223> OTHER INFORMATION: S. cohnii femA capture sequence

<400> SEQUENCE: 44
acttaacact tcacgctctg acttgag                                              27

<210> SEQ ID NO 45
<211> LENGTH: 27
<212> TYPE: DNA
<213> ORGANISM: Artificial Sequence
<220> FEATURE:
<223> OTHER INFORMATION: S. gallinarum femA capture sequence

<400> SEQUENCE: 45
acttaaaact tcacgttcag cagtaag                                              27

<210> SEQ ID NO 46
<211> LENGTH: 27
<212> TYPE: DNA
<213> ORGANISM: Artificial Sequence
<220> FEATURE:
<223> OTHER INFORMATION: S. intermedius femA capture sequence

<400> SEQUENCE: 46
gtggaaatct tgctcttcag atttcag                                              27

<210> SEQ ID NO 47
<211> LENGTH: 27
<212> TYPE: DNA
<213> ORGANISM: Artificial Sequence
<220> FEATURE:
<223> OTHER INFORMATION: S. lugdunensis femA capture sequence

<400> SEQUENCE: 47
```
ttctaaagtt tgtcgttcat tcgttag                                27

<210> SEQ ID NO 48
<211> LENGTH: 27
<212> TYPE: DNA
<213> ORGANISM: Artificial Sequence
<220> FEATURE:
<223> OTHER INFORMATION: S. schleiferi femA capture sequence

<400> SEQUENCE: 48
tttaaagtct tgcgcttcag tgttgag                                27

<210> SEQ ID NO 49
<211> LENGTH: 27
<212> TYPE: DNA
<213> ORGANISM: Artificial Sequence
<220> FEATURE:
<223> OTHER INFORMATION: S. sciuri femA capture sequence

<400> SEQUENCE: 49
gttgtattgt tcatgttctt tttctaa                                27

<210> SEQ ID NO 50
<211> LENGTH: 27
<212> TYPE: DNA
<213> ORGANISM: Artificial Sequence
<220> FEATURE:
<223> OTHER INFORMATION: S. simulans femA capture sequence

<400> SEQUENCE: 50
ttctaaattc ttttgttcag cgttcaa                                27

<210> SEQ ID NO 51
<211> LENGTH: 27
<212> TYPE: DNA
<213> ORGANISM: Artificial Sequence
<220> FEATURE:
<223> OTHER INFORMATION: S. warneri femA capture sequence

<400> SEQUENCE: 51
agttaaggtt tctttttcat tattgag                                27

<210> SEQ ID NO 52
<211> LENGTH: 27
<212> TYPE: DNA
<213> ORGANISM: Artificial Sequence
<220> FEATURE:
<223> OTHER INFORMATION: S. xylosis femA capture sequence

<400> SEQUENCE: 52
gcttaacacc tcacgttgag cttgcaa                                27

<210> SEQ ID NO 53
<211> LENGTH: 20
<212> TYPE: DNA
<213> ORGANISM: Artificial Sequence
<220> FEATURE:
<223> OTHER INFORMATION: consensus primer MycU4 sense

<400> SEQUENCE: 53
catgcagtga attagaacgt                                        20

<210> SEQ ID NO 54
<211> LENGTH: 18
<212> TYPE: DNA
<213> ORGANISM: Artificial Sequence

```
<220> FEATURE:
<223> OTHER INFORMATION: consensus primer APmcon02 antisense

<400> SEQUENCE: 54
gtasgtcatr rstyctcc                                                 18

<210> SEQ ID NO 55
<211> LENGTH: 21
<212> TYPE: DNA
<213> ORGANISM: Artificial Sequence
<220> FEATURE:
<223> OTHER INFORMATION: Mycobacteria avium capture probe

<400> SEQUENCE: 55
cggtcgtctc cgaagcccgc g                                             21

<210> SEQ ID NO 56
<211> LENGTH: 20
<212> TYPE: DNA
<213> ORGANISM: Artificial Sequence
<220> FEATURE:
<223> OTHER INFORMATION: Mycobacteria gastrii 1 capture probe

<400> SEQUENCE: 56
gatcggcagc ggtgccgggg                                               20

<210> SEQ ID NO 57
<211> LENGTH: 19
<212> TYPE: DNA
<213> ORGANISM: Artificial Sequence
<220> FEATURE:
<223> OTHER INFORMATION: Mycobacteria gastrii 3 capture probe

<400> SEQUENCE: 57
gtatcgcggg cggcaaggt                                                19

<210> SEQ ID NO 58
<211> LENGTH: 24
<212> TYPE: DNA
<213> ORGANISM: Artificial Sequence
<220> FEATURE:
<223> OTHER INFORMATION: Mycobacteria gastrii 5 capture probe

<400> SEQUENCE: 58
tctgccgatc ggcagcggtg ccgg                                          24

<210> SEQ ID NO 59
<211> LENGTH: 24
<212> TYPE: DNA
<213> ORGANISM: Artificial Sequence
<220> FEATURE:
<223> OTHER INFORMATION: Mycobacteria gastrii 7 capture probe

<400> SEQUENCE: 59
gccggggccg gtattcgcgg gcgg                                          24

<210> SEQ ID NO 60
<211> LENGTH: 22
<212> TYPE: DNA
<213> ORGANISM: Artificial Sequence
<220> FEATURE:
<223> OTHER INFORMATION: Mycobacteria gordonae capture probe

<400> SEQUENCE: 60
gacgggcact agttgtcaga gg                                            22
```

<210> SEQ ID NO 61
<211> LENGTH: 21
<212> TYPE: DNA
<213> ORGANISM: Artificial Sequence
<220> FEATURE:
<223> OTHER INFORMATION: Mycobacterium intracellulare 1 capture probe

<400> SEQUENCE: 61
gggccgccgg gggcctcgcc g                                      21

<210> SEQ ID NO 62
<211> LENGTH: 21
<212> TYPE: DNA
<213> ORGANISM: Artificial Sequence
<220> FEATURE:
<223> OTHER INFORMATION: Mycobacterium intracellulare 3 capture probe

<400> SEQUENCE: 62
gcctcgccgc ccaagacagt g                                      21

<210> SEQ ID NO 63
<211> LENGTH: 21
<212> TYPE: DNA
<213> ORGANISM: Artificial Sequence
<220> FEATURE:
<223> OTHER INFORMATION: Mycobacterium leprae capture probe

<400> SEQUENCE: 63
gatttcggcg tccatcggtg g                                      21

<210> SEQ ID NO 64
<211> LENGTH: 21
<212> TYPE: DNA
<213> ORGANISM: Artificial Sequence
<220> FEATURE:
<223> OTHER INFORMATION: Mycobacterium kansasi 1 capture probe

<400> SEQUENCE: 64
gatcgtcggc agtggtgacg g                                      21

<210> SEQ ID NO 65
<211> LENGTH: 17
<212> TYPE: DNA
<213> ORGANISM: Artificial Sequence
<220> FEATURE:
<223> OTHER INFORMATION: Mycobacterium kansasi 3 capture probe

<400> SEQUENCE: 65
tcgtcggcag tggtgac                                           17

<210> SEQ ID NO 66
<211> LENGTH: 27
<212> TYPE: DNA
<213> ORGANISM: Artificial Sequence
<220> FEATURE:
<223> OTHER INFORMATION: Mycobacterium kansasi 5 capture probe

<400> SEQUENCE: 66
atccgccgat cgtcggcagt ggtgacg                                27

<210> SEQ ID NO 67
<211> LENGTH: 21
<212> TYPE: DNA
<213> ORGANISM: Artificial Sequence
<220> FEATURE:
<223> OTHER INFORMATION: Mycobacterium malmoense capture probe

<400> SEQUENCE: 67
gacccacaac actggtcggc g                                    21

<210> SEQ ID NO 68
<211> LENGTH: 21
<212> TYPE: DNA
<213> ORGANISM: Artificial Sequence
<220> FEATURE:
<223> OTHER INFORMATION: Mycobacterium marinum capture probe

<400> SEQUENCE: 68
cggaggtgat ggcgctggtc g                                    21

<210> SEQ ID NO 69
<211> LENGTH: 20
<212> TYPE: DNA
<213> ORGANISM: Artificial Sequence
<220> FEATURE:
<223> OTHER INFORMATION: Mycobacterium scrofulaceum capture probe

<400> SEQUENCE: 69
cggcggcacg gatcggcgtc                                      20

<210> SEQ ID NO 70
<211> LENGTH: 20
<212> TYPE: DNA
<213> ORGANISM: Artificial Sequence
<220> FEATURE:
<223> OTHER INFORMATION: Mycobacterium simiae capture probe

<400> SEQUENCE: 70
atcgctcctg gtcgcgccta                                      20

<210> SEQ ID NO 71
<211> LENGTH: 21
<212> TYPE: DNA
<213> ORGANISM: Artificial Sequence
<220> FEATURE:
<223> OTHER INFORMATION: Mycobacterium szulgai capture probe

<400> SEQUENCE: 71
cccggcgcga ccagcagaac g                                    21

<210> SEQ ID NO 72
<211> LENGTH: 22
<212> TYPE: DNA
<213> ORGANISM: Artificial Sequence
<220> FEATURE:
<223> OTHER INFORMATION: Mycobacterium tuberculosis capture probe

<400> SEQUENCE: 72
gccgtccagt cgttaatgtc gc                                   22

<210> SEQ ID NO 73
<211> LENGTH: 22
<212> TYPE: DNA
<213> ORGANISM: Artificial Sequence
<220> FEATURE:
<223> OTHER INFORMATION: Mycobacterium xenopi capture probe

<400> SEQUENCE: 73
cggtagaagc tgcgatgaca cg                                   22

<210> SEQ ID NO 74

```
<210> SEQ ID NO 74
<211> LENGTH: 24
<212> TYPE: DNA
<213> ORGANISM: Artificial Sequence
<220> FEATURE:
<223> OTHER INFORMATION: consensus primer DPSCONS2 sense

<400> SEQUENCE: 74
gggctccagc agccaagaag agga                                          24

<210> SEQ ID NO 75
<211> LENGTH: 24
<212> TYPE: DNA
<213> ORGANISM: Artificial Sequence
<220> FEATURE:
<223> OTHER INFORMATION: consensus primer DPSMAGE1 sense

<400> SEQUENCE: 75
gggttccagc agccgtgaag agga                                          24

<210> SEQ ID NO 76
<211> LENGTH: 24
<212> TYPE: DNA
<213> ORGANISM: Artificial Sequence
<220> FEATURE:
<223> OTHER INFORMATION: consensus primer DPSMAG8 sense

<400> SEQUENCE: 76
gggttccagc agcaatgaag agga                                          24

<210> SEQ ID NO 77
<211> LENGTH: 24
<212> TYPE: DNA
<213> ORGANISM: Artificial Sequence
<220> FEATURE:
<223> OTHER INFORMATION: consensus primer DPSMAG12 sense

<400> SEQUENCE: 77
gggctccagc aacgaagaac agga                                          24

<210> SEQ ID NO 78
<211> LENGTH: 24
<212> TYPE: DNA
<213> ORGANISM: Artificial Sequence
<220> FEATURE:
<223> OTHER INFORMATION: consensus primer DPASCONB4 antisense

<400> SEQUENCE: 78
cggtactcca ggtagttttc ctgc                                          24

<210> SEQ ID NO 79
<211> LENGTH: 27
<212> TYPE: DNA
<213> ORGANISM: Artificial Sequence
<220> FEATURE:
<223> OTHER INFORMATION: capture probe Mage 1 DTAS01

<400> SEQUENCE: 79
acaaggactc caggatacaa gaggtgc                                       27

<210> SEQ ID NO 80
<211> LENGTH: 27
<212> TYPE: DNA
<213> ORGANISM: Artificial Sequence
<220> FEATURE:
<223> OTHER INFORMATION: capture probe Mage 2 DTAS02

<400> SEQUENCE: 80
```
actcggactc caggtcggga aacattc    27

<210> SEQ ID NO 81
<211> LENGTH: 27
<212> TYPE: DNA
<213> ORGANISM: Artificial Sequence
<220> FEATURE:
<223> OTHER INFORMATION: capture probe Mage 3 DTS0306

<400> SEQUENCE: 81
aagacagtat cttgggggat cccaaga    27

<210> SEQ ID NO 82
<211> LENGTH: 27
<212> TYPE: DNA
<213> ORGANISM: Artificial Sequence
<220> FEATURE:
<223> OTHER INFORMATION: capture probe Mage 4 DTAS04

<400> SEQUENCE: 82
tcggaacaag gactctgcgt caggcga    27

<210> SEQ ID NO 83
<211> LENGTH: 27
<212> TYPE: DNA
<213> ORGANISM: Artificial Sequence
<220> FEATURE:
<223> OTHER INFORMATION: capture probe Mage 5 DTAS05

<400> SEQUENCE: 83
gctcggaaca cagactctgg gtcaggg    27

<210> SEQ ID NO 84
<211> LENGTH: 27
<212> TYPE: DNA
<213> ORGANISM: Artificial Sequence
<220> FEATURE:
<223> OTHER INFORMATION: capture probe Mage 6 DTS06

<400> SEQUENCE: 84
caagacaggc ttcctgataa tcatcct    27

<210> SEQ ID NO 85
<211> LENGTH: 27
<212> TYPE: DNA
<213> ORGANISM: Artificial Sequence
<220> FEATURE:
<223> OTHER INFORMATION: capture probe Mage 7 DTAS07

<400> SEQUENCE: 85
aggacgccag gtgagcgggg tgtgtct    27

<210> SEQ ID NO 86
<211> LENGTH: 27
<212> TYPE: DNA
<213> ORGANISM: Artificial Sequence
<220> FEATURE:
<223> OTHER INFORMATION: capture probe Mage 8 DTAS08

<400> SEQUENCE: 86
gggactccag gtgagctggg tccgggg    27

<210> SEQ ID NO 87
<211> LENGTH: 27
<212> TYPE: DNA

<213> ORGANISM: Artificial Sequence
<220> FEATURE:
<223> OTHER INFORMATION: capture probe Mage 9 DTAS09

<400> SEQUENCE: 87
tgaactccag ctgagctggg tcgaccg                               27

<210> SEQ ID NO 88
<211> LENGTH: 27
<212> TYPE: DNA
<213> ORGANISM: Artificial Sequence
<220> FEATURE:
<223> OTHER INFORMATION: capture probe Mage 10 DTAS10

<400> SEQUENCE: 88
tgggtaaaga ctcactgtct ggcagga                               27

<210> SEQ ID NO 89
<211> LENGTH: 27
<212> TYPE: DNA
<213> ORGANISM: Artificial Sequence
<220> FEATURE:
<223> OTHER INFORMATION: capture probe Mage 11 DTAS11

<400> SEQUENCE: 89
gaaaaggact cagggtctat caggtca                               27

<210> SEQ ID NO 90
<211> LENGTH: 27
<212> TYPE: DNA
<213> ORGANISM: Artificial Sequence
<220> FEATURE:
<223> OTHER INFORMATION: capture probe Mage 12 DTAS12

<400> SEQUENCE: 90
gtgctacttg gaagctcgtc tccaggt                               27

<210> SEQ ID NO 91
<211> LENGTH: 22
<212> TYPE: DNA
<213> ORGANISM: Artificial Sequence
<220> FEATURE:
<223> OTHER INFORMATION: consensus primer CONSENSUS2-3-4 sense

<400> SEQUENCE: 91
tgcagacmac caccaactac tt                                    22

<210> SEQ ID NO 92
<211> LENGTH: 22
<212> TYPE: DNA
<213> ORGANISM: Artificial Sequence
<220> FEATURE:
<223> OTHER INFORMATION: consensus primer CONSENSUS1-5 sense

<400> SEQUENCE: 92
tgmggkccaa gatgaccaac wt                                    22

<210> SEQ ID NO 93
<211> LENGTH: 22
<212> TYPE: DNA
<213> ORGANISM: Artificial Sequence
<220> FEATURE:
<223> OTHER INFORMATION: consensus primer CONSENSUS1-5 antisense

<400> SEQUENCE: 93
tcatgrcrca saggttcagg at                                    22

<210> SEQ ID NO 94
<211> LENGTH: 27
<212> TYPE: DNA
<213> ORGANISM: Artificial Sequence
<220> FEATURE:
<223> OTHER INFORMATION: capture probe DRD1

<400> SEQUENCE: 94
ctggcttttg gcctttgggt ccctttt                                27

<210> SEQ ID NO 95
<211> LENGTH: 27
<212> TYPE: DNA
<213> ORGANISM: Artificial Sequence
<220> FEATURE:
<223> OTHER INFORMATION: capture probe DRD2

<400> SEQUENCE: 95
tgattggaaa ttcagcagga ttcactg                                27

<210> SEQ ID NO 96
<211> LENGTH: 27
<212> TYPE: DNA
<213> ORGANISM: Artificial Sequence
<220> FEATURE:
<223> OTHER INFORMATION: capture probe DRD3

<400> SEQUENCE: 96
gagtctggaa tttcagccgc atttgct                                27

<210> SEQ ID NO 97
<211> LENGTH: 27
<212> TYPE: DNA
<213> ORGANISM: Artificial Sequence
<220> FEATURE:
<223> OTHER INFORMATION: capture probe DRD4

<400> SEQUENCE: 97
cgtctggctg ctgagccccc gcctctg                                27

<210> SEQ ID NO 98
<211> LENGTH: 27
<212> TYPE: DNA
<213> ORGANISM: Artificial Sequence
<220> FEATURE:
<223> OTHER INFORMATION: capture probe DRD5

<400> SEQUENCE: 98
ctgggtactg gcccctttggg acattct                               27

<210> SEQ ID NO 99
<211> LENGTH: 18
<212> TYPE: DNA
<213> ORGANISM: Artificial Sequence
<220> FEATURE:
<223> OTHER INFORMATION: primer H1sense

<400> SEQUENCE: 99
ctccgtccag caacccct                                          18

<210> SEQ ID NO 100
<211> LENGTH: 19
<212> TYPE: DNA
<213> ORGANISM: Artificial Sequence
<220> FEATURE:

<223> OTHER INFORMATION: primer H2sense

<400> SEQUENCE: 100
ctgtgctggt cacccagt                                                    19

<210> SEQ ID NO 101
<211> LENGTH: 21
<212> TYPE: DNA
<213> ORGANISM: Artificial Sequence
<220> FEATURE:
<223> OTHER INFORMATION: primer H3sense

<400> SEQUENCE: 101
actcatcagc tatgaccgat t                                                21

<210> SEQ ID NO 102
<211> LENGTH: 20
<212> TYPE: DNA
<213> ORGANISM: Artificial Sequence
<220> FEATURE:
<223> OTHER INFORMATION: primer H1antisense

<400> SEQUENCE: 102
accttccttg gtatcgtctg                                                  20

<210> SEQ ID NO 103
<211> LENGTH: 21
<212> TYPE: DNA
<213> ORGANISM: Artificial Sequence
<220> FEATURE:
<223> OTHER INFORMATION: primer H2 antisense

<400> SEQUENCE: 103
gaaaccagca gatgatgaac g                                                21

<210> SEQ ID NO 104
<211> LENGTH: 19
<212> TYPE: DNA
<213> ORGANISM: Artificial Sequence
<220> FEATURE:
<223> OTHER INFORMATION: primer H3 antisense

<400> SEQUENCE: 104
gcatctggtg ggggttctg                                                   19

<210> SEQ ID NO 105
<211> LENGTH: 18
<212> TYPE: DNA
<213> ORGANISM: Artificial Sequence
<220> FEATURE:
<223> OTHER INFORMATION: capture probe H1

<400> SEQUENCE: 105
ccccaggatg gtagcgga                                                    18

<210> SEQ ID NO 106
<211> LENGTH: 22
<212> TYPE: DNA
<213> ORGANISM: Artificial Sequence
<220> FEATURE:
<223> OTHER INFORMATION: capture probe H2

<400> SEQUENCE: 106
aggatagggt gatagaaata ac                                               22

```
<210> SEQ ID NO 107
<211> LENGTH: 18
<212> TYPE: DNA
<213> ORGANISM: Artificial Sequence
<220> FEATURE:
<223> OTHER INFORMATION: capture probe H3

<400> SEQUENCE: 107
tctcgtgtcc ccctgctg                                              18

<210> SEQ ID NO 108
<211> LENGTH: 20
<212> TYPE: DNA
<213> ORGANISM: Artificial Sequence
<220> FEATURE:
<223> OTHER INFORMATION: general consensus primer sequence for subtypes
      1A, 1B, 1C, 1D, 1E, 2A, 2B, 2C, 4, 6, and 7 sense

<400> SEQUENCE: 108
atchtgcacc tstgbgbcat                                            20

<210> SEQ ID NO 109
<211> LENGTH: 20
<212> TYPE: DNA
<213> ORGANISM: Artificial Sequence
<220> FEATURE:
<223> OTHER INFORMATION: consensus primer for subtype 1A sense

<400> SEQUENCE: 109
atcctgcacc tgtgcgccat                                            20

<210> SEQ ID NO 110
<211> LENGTH: 20
<212> TYPE: DNA
<213> ORGANISM: Artificial Sequence
<220> FEATURE:
<223> OTHER INFORMATION: consensus primer for subtype 1B sense

<400> SEQUENCE: 110
atcatgcatc tctgtgtcat                                            20

<210> SEQ ID NO 111
<211> LENGTH: 20
<212> TYPE: DNA
<213> ORGANISM: Artificial Sequence
<220> FEATURE:
<223> OTHER INFORMATION: consensus primer for subtype 1C sense

<400> SEQUENCE: 111
atcatgcacc tctgcgccat                                            20

<210> SEQ ID NO 112
<211> LENGTH: 20
<212> TYPE: DNA
<213> ORGANISM: Artificial Sequence
<220> FEATURE:
<223> OTHER INFORMATION: consensus primer for subtype 1D sense

<400> SEQUENCE: 112
atcctgcatc tctgtgtcat                                            20

<210> SEQ ID NO 113
<211> LENGTH: 20
<212> TYPE: DNA
<213> ORGANISM: Artificial Sequence
<220> FEATURE:
<223> OTHER INFORMATION: consensus primer for subtype 1E sense
```

<400> SEQUENCE: 113
atcttgcacc tgtcggctat					20

<210> SEQ ID NO 114
<211> LENGTH: 20
<212> TYPE: DNA
<213> ORGANISM: Artificial Sequence
<220> FEATURE:
<223> OTHER INFORMATION: consensus primer for subtype 2A sense

<400> SEQUENCE: 114
atcatgcacc tctgcgccat					20

<210> SEQ ID NO 115
<211> LENGTH: 20
<212> TYPE: DNA
<213> ORGANISM: Artificial Sequence
<220> FEATURE:
<223> OTHER INFORMATION: consensus primer for subtype 2B sense

<400> SEQUENCE: 115
atcatgcatc tctgtgccat					20

<210> SEQ ID NO 116
<211> LENGTH: 20
<212> TYPE: DNA
<213> ORGANISM: Artificial Sequence
<220> FEATURE:
<223> OTHER INFORMATION: consensus primer for subtype 2C sense

<400> SEQUENCE: 116
atcatgcacc tctgcgccat					20

<210> SEQ ID NO 117
<211> LENGTH: 20
<212> TYPE: DNA
<213> ORGANISM: Artificial Sequence
<220> FEATURE:
<223> OTHER INFORMATION: consensus primer for subtype 4 sense

<400> SEQUENCE: 117 attttttcacc tctgctgcat					20

<210> SEQ ID NO 118
<211> LENGTH: 20
<212> TYPE: DNA
<213> ORGANISM: Artificial Sequence
<220> FEATURE:
<223> OTHER INFORMATION: consensus primer for subtype 6 sense

<400> SEQUENCE: 118
atcctcaacc tctgcttcat					20

<210> SEQ ID NO 119
<211> LENGTH: 20
<212> TYPE: DNA
<213> ORGANISM: Artificial Sequence
<220> FEATURE:
<223> OTHER INFORMATION: consensus primer for subtype 7 sense

<400> SEQUENCE: 119
atcatgaccc tgtgcgtgat					20

<210> SEQ ID NO 120

```
<211> LENGTH: 20
<212> TYPE: DNA
<213> ORGANISM: Artificial Sequence
<220> FEATURE:
<223> OTHER INFORMATION: general consensus primer for 4, 6

<400> SEQUENCE: 120
atcytycacc tctgcykcat                                                    20

<210> SEQ ID NO 121
<211> LENGTH: 20
<212> TYPE: DNA
<213> ORGANISM: Artificial Sequence
<220> FEATURE:
<223> OTHER INFORMATION: consensus primer for 4

<400> SEQUENCE: 121
atttttcacc tctgctgcat                                                    20

<210> SEQ ID NO 122
<211> LENGTH: 20
<212> TYPE: DNA
<213> ORGANISM: Artificial Sequence
<220> FEATURE:
<223> OTHER INFORMATION: consensus primer for 6

<400> SEQUENCE: 122
atttttcacc tctgctgcat                                                    20

<210> SEQ ID NO 123
<211> LENGTH: 20
<212> TYPE: DNA
<213> ORGANISM: Artificial Sequence
<220> FEATURE:
<223> OTHER INFORMATION: general consensus primer for 5A, 5B

<400> SEQUENCE: 123
atctggaayg tgrcagccat                                                    20

<210> SEQ ID NO 124
<211> LENGTH: 20
<212> TYPE: DNA
<213> ORGANISM: Artificial Sequence
<220> FEATURE:
<223> OTHER INFORMATION: consensus primer for 5A

<400> SEQUENCE: 124
atctggaatg tgacagcaat                                                    20

<210> SEQ ID NO 125
<211> LENGTH: 20
<212> TYPE: DNA
<213> ORGANISM: Artificial Sequence
<220> FEATURE:
<223> OTHER INFORMATION: consensus primer for 5B

<400> SEQUENCE: 125
atctggaacg tggcggccat                                                    20

<210> SEQ ID NO 126
<211> LENGTH: 20
<212> TYPE: DNA
<213> ORGANISM: Artificial Sequence
<220> FEATURE:
<223> OTHER INFORMATION: consensus primer for Specific 7

<400> SEQUENCE: 126
```
atcatgaccc tgtgcgtgat                                                    20

<210> SEQ ID NO 127
<211> LENGTH: 19
<212> TYPE: DNA
<213> ORGANISM: Artificial Sequence
<220> FEATURE:
<223> OTHER INFORMATION: consensus primer for Specific 3B

<400> SEQUENCE: 127
cttccggaac gattagaaa                                                     19

<210> SEQ ID NO 128
<211> LENGTH: 17
<212> TYPE: DNA
<213> ORGANISM: Artificial Sequence
<220> FEATURE:
<223> OTHER INFORMATION: general consensus primer for Consensus subtypes
      1A, 1B, 1C, 1D, 1E, 2A, 2B, 2C, 4, 7
<221> NAME/KEY: misc_feature
<222> LOCATION: (1)...(17)
<223> OTHER INFORMATION: n = A,T,C or G

<400> SEQUENCE: 128
ttgghngcyt tcygbtc                                                       17

<210> SEQ ID NO 129
<211> LENGTH: 17
<212> TYPE: DNA
<213> ORGANISM: Artificial Sequence
<220> FEATURE:
<223> OTHER INFORMATION: consensus primer Consensus subtype 1A antisense

<400> SEQUENCE: 129
ttcaccgtct tcctttc                                                       17

<210> SEQ ID NO 130
<211> LENGTH: 17
<212> TYPE: DNA
<213> ORGANISM: Artificial Sequence
<220> FEATURE:
<223> OTHER INFORMATION: consensus primer for Consensus subtype 1B
      antisense

<400> SEQUENCE: 130
ttggtggctt tgcgctc                                                       17

<210> SEQ ID NO 131
<211> LENGTH: 17
<212> TYPE: DNA
<213> ORGANISM: Artificial Sequence
<220> FEATURE:
<223> OTHER INFORMATION: consensus primer for Consensus subtype 1C
      antisense

<400> SEQUENCE: 131
ttggaagctt tcttttc                                                       17

<210> SEQ ID NO 132
<211> LENGTH: 17
<212> TYPE: DNA
<213> ORGANISM: Artificial Sequence
<220> FEATURE:
<223> OTHER INFORMATION: consensus primer for Consensus subtype 1D
      antisense

<400> SEQUENCE: 132
ttagtggctt tcctttc                                                17

<210> SEQ ID NO 133
<211> LENGTH: 17
<212> TYPE: DNA
<213> ORGANISM: Artificial Sequence
<220> FEATURE:
<223> OTHER INFORMATION: consensus primer for Consensus subtype 1E
      antisense

<400> SEQUENCE: 133
gtggctgctt tgcgttc                                                17

<210> SEQ ID NO 134
<211> LENGTH: 17
<212> TYPE: DNA
<213> ORGANISM: Artificial Sequence
<220> FEATURE:
<223> OTHER INFORMATION: consensus primer for Consensus subtype 2A
      antisense

<400> SEQUENCE: 134
ttgcacgcct tttgctc                                                17

<210> SEQ ID NO 135
<211> LENGTH: 17
<212> TYPE: DNA
<213> ORGANISM: Artificial Sequence
<220> FEATURE:
<223> OTHER INFORMATION: consensus primer for Consensus subtype 2B
      antisense

<400> SEQUENCE: 135
tttgaggctc tctgttc                                                17

<210> SEQ ID NO 136
<211> LENGTH: 17
<212> TYPE: DNA
<213> ORGANISM: Artificial Sequence
<220> FEATURE:
<223> OTHER INFORMATION: consensus primer for Consensus subtype 2C
      antisense

<400> SEQUENCE: 136
ttggaagctt tcttttc                                                17

<210> SEQ ID NO 137
<211> LENGTH: 17
<212> TYPE: DNA
<213> ORGANISM: Artificial Sequence
<220> FEATURE:
<223> OTHER INFORMATION: consensus primer for Consensus subtype 4
      antisense

<400> SEQUENCE: 137
ttggctgctt tccggtc                                                17

<210> SEQ ID NO 138
<211> LENGTH: 17
<212> TYPE: DNA
<213> ORGANISM: Artificial Sequence
<220> FEATURE:
<223> OTHER INFORMATION: consensus primer for Consensus subtype 7
      antisense

<400> SEQUENCE: 138

```
gtggctgctt tctgttc                                                17
```

<210> SEQ ID NO 139
<211> LENGTH: 17
<212> TYPE: DNA
<213> ORGANISM: Artificial Sequence
<220> FEATURE:
<223> OTHER INFORMATION: consensus primer for Consensus Specific 1A
      antisense

<400> SEQUENCE: 139

```
ttcaccgtct tcctttc                                                17
```

<210> SEQ ID NO 140
<211> LENGTH: 17
<212> TYPE: DNA
<213> ORGANISM: Artificial Sequence
<220> FEATURE:
<223> OTHER INFORMATION: consensus primer for Consensus Specific 4
      antisense

<400> SEQUENCE: 140

```
tcttggctgc tttggtc                                                17
```

<210> SEQ ID NO 141
<211> LENGTH: 18
<212> TYPE: DNA
<213> ORGANISM: Artificial Sequence
<220> FEATURE:
<223> OTHER INFORMATION: consensus primer for Consensus Specific 6
      antisense

<400> SEQUENCE: 141

```
ataaagagcg ggtagatg                                               18
```

<210> SEQ ID NO 142
<211> LENGTH: 16
<212> TYPE: DNA
<213> ORGANISM: Artificial Sequence
<220> FEATURE:
<223> OTHER INFORMATION: consensus primer Consensus 5A,5B antisense

<400> SEQUENCE: 142

```
ccttctgctc cctcca                                                 16
```

<210> SEQ ID NO 143
<211> LENGTH: 16
<212> TYPE: DNA
<213> ORGANISM: Artificial Sequence
<220> FEATURE:
<223> OTHER INFORMATION: consensus primer for Consensus 5A antisense

<400> SEQUENCE: 143

```
ccttctgttc cctcca                                                 16
```

<210> SEQ ID NO 144
<211> LENGTH: 16
<212> TYPE: DNA
<213> ORGANISM: Artificial Sequence
<220> FEATURE:
<223> OTHER INFORMATION: consensus primer for Consensus 5B antisense

<400> SEQUENCE: 144

```
ccttctgctc ccgcca                                                 16
```

<210> SEQ ID NO 145

```
<211> LENGTH: 16
<212> TYPE: DNA
<213> ORGANISM: Artificial Sequence
<220> FEATURE:
<223> OTHER INFORMATION: consensus primer for Specific 3B antisense

<400> SEQUENCE: 145
accggggact ctgtgt                                                    16

<210> SEQ ID NO 146
<211> LENGTH: 21
<212> TYPE: DNA
<213> ORGANISM: Artificial Sequence
<220> FEATURE:
<223> OTHER INFORMATION: capture probe HTR1C

<400> SEQUENCE: 146
ctatgctcaa taggattacg t                                              21

<210> SEQ ID NO 147
<211> LENGTH: 19
<212> TYPE: DNA
<213> ORGANISM: Artificial Sequence
<220> FEATURE:
<223> OTHER INFORMATION: capture probe HTR2A

<400> SEQUENCE: 147
gtggtgaatg gggttctgg                                                 19

<210> SEQ ID NO 148
<211> LENGTH: 21
<212> TYPE: DNA
<213> ORGANISM: Artificial Sequence
<220> FEATURE:
<223> OTHER INFORMATION: capture probe HTR2B

<400> SEQUENCE: 148
tggcctgaat tggctttttg a                                              21

<210> SEQ ID NO 149
<211> LENGTH: 22
<212> TYPE: DNA
<213> ORGANISM: Artificial Sequence
<220> FEATURE:
<223> OTHER INFORMATION: capture probe HTR2C/1C

<400> SEQUENCE: 149
ttattcacga acactttgct tt                                             22

<210> SEQ ID NO 150
<211> LENGTH: 20
<212> TYPE: DNA
<213> ORGANISM: Artificial Sequence
<220> FEATURE:
<223> OTHER INFORMATION: capture probe HTR1B

<400> SEQUENCE: 150
aatagtccac cgcatcagtg                                                20

<210> SEQ ID NO 151
<211> LENGTH: 19
<212> TYPE: DNA
<213> ORGANISM: Artificial Sequence
<220> FEATURE:
<223> OTHER INFORMATION: capture probe HTR1D

<400> SEQUENCE: 151
```

```
gtactccagg gcatcggtg                                                    19

<210> SEQ ID NO 152
<211> LENGTH: 20
<212> TYPE: DNA
<213> ORGANISM: Artificial Sequence
<220> FEATURE:
<223> OTHER INFORMATION: capture probe HTR1A

<400> SEQUENCE: 152
catagtctat agggtcggtg                                                   20

<210> SEQ ID NO 153
<211> LENGTH: 20
<212> TYPE: DNA
<213> ORGANISM: Artificial Sequence
<220> FEATURE:
<223> OTHER INFORMATION: capture probe HTR1E

<400> SEQUENCE: 153
atactcgact gcgtctgtga                                                   20

<210> SEQ ID NO 154
<211> LENGTH: 19
<212> TYPE: DNA
<213> ORGANISM: Artificial Sequence
<220> FEATURE:
<223> OTHER INFORMATION: capture probe HTR7

<400> SEQUENCE: 154
gtacgtgagg ggtctcgtg                                                    19

<210> SEQ ID NO 155
<211> LENGTH: 19
<212> TYPE: DNA
<213> ORGANISM: Artificial Sequence
<220> FEATURE:
<223> OTHER INFORMATION: capture probe HTR5A

<400> SEQUENCE: 155
ggcgcgttat tgaccagta                                                    19

<210> SEQ ID NO 156
<211> LENGTH: 18
<212> TYPE: DNA
<213> ORGANISM: Artificial Sequence
<220> FEATURE:
<223> OTHER INFORMATION: capture probe HTR5B

<400> SEQUENCE: 156
ggcgcgtgat agtccagt                                                     18

<210> SEQ ID NO 157
<211> LENGTH: 21
<212> TYPE: DNA
<213> ORGANISM: Artificial Sequence
<220> FEATURE:
<223> OTHER INFORMATION: capture probe HTR3B

<400> SEQUENCE: 157
gatatcaaag gggaaagcgt a                                                 21

<210> SEQ ID NO 158
<211> LENGTH: 20
<212> TYPE: DNA
```

```
<213> ORGANISM: Artificial Sequence
<220> FEATURE:
<223> OTHER INFORMATION: capture probe HTR4

<400> SEQUENCE: 158
aaaccaaagg ttgacagcag                                              20

<210> SEQ ID NO 159
<211> LENGTH: 18
<212> TYPE: DNA
<213> ORGANISM: Artificial Sequence
<220> FEATURE:
<223> OTHER INFORMATION: capture probe HTR6

<400> SEQUENCE: 159
gtagcgcagc ggcgagag                                                18

<210> SEQ ID NO 160
<211> LENGTH: 20
<212> TYPE: DNA
<213> ORGANISM: Artificial Sequence
<220> FEATURE:
<223> OTHER INFORMATION: consensus primer IPSCONA sense

<400> SEQUENCE: 160
gacagcgacg ccgcgagcca                                              20

<210> SEQ ID NO 161
<211> LENGTH: 22
<212> TYPE: DNA
<213> ORGANISM: Artificial Sequence
<220> FEATURE:
<223> OTHER INFORMATION: consensus primer IPASCONA antisense

<400> SEQUENCE: 161
cgtgtcctgg gtctggtcct cc                                           22

<210> SEQ ID NO 162
<211> LENGTH: 27
<212> TYPE: DNA
<213> ORGANISM: Artificial Sequence
<220> FEATURE:
<223> OTHER INFORMATION: capture probe HLA-A1 ITSA01

<400> SEQUENCE: 162
ggagggccgg tgcgtggacg ggctccg                                      27

<210> SEQ ID NO 163
<211> LENGTH: 27
<212> TYPE: DNA
<213> ORGANISM: Artificial Sequence
<220> FEATURE:
<223> OTHER INFORMATION: capture probe HLA-A2 ITSASA02

<400> SEQUENCE: 163
tctccccgtc ccaatactcc ggaccct                                      27

<210> SEQ ID NO 164
<211> LENGTH: 27
<212> TYPE: DNA
<213> ORGANISM: Artificial Sequence
<220> FEATURE:
<223> OTHER INFORMATION: capture probe HLA-A3 ITASA03A

<400> SEQUENCE: 164
ctgggccttc acattccgtg tctcctg                                      27
```

<210> SEQ ID NO 165
<211> LENGTH: 27
<212> TYPE: DNA
<213> ORGANISM: Artificial Sequence
<220> FEATURE:
<223> OTHER INFORMATION: capture probe HLA-A3 ITSA03B

<400> SEQUENCE: 165
agcgcaagtg ggaggcggcc catgagg                                27

<210> SEQ ID NO 166
<211> LENGTH: 27
<212> TYPE: DNA
<213> ORGANISM: Artificial Sequence
<220> FEATURE:
<223> OTHER INFORMATION: capture probe HLA-A11 ITSA11A

<400> SEQUENCE: 166
gcccatgcgg cggagcagca gagagcc                                27

<210> SEQ ID NO 167
<211> LENGTH: 27
<212> TYPE: DNA
<213> ORGANISM: Artificial Sequence
<220> FEATURE:
<223> OTHER INFORMATION: capture probe HLA-A11 ITSA11B

<400> SEQUENCE: 167
cctggagggc cggtgcgtgg agtggct                                27

<210> SEQ ID NO 168
<211> LENGTH: 27
<212> TYPE: DNA
<213> ORGANISM: Artificial Sequence
<220> FEATURE:
<223> OTHER INFORMATION: capture probe HLA-A23 ITSA23A

<400> SEQUENCE: 168
gcccgtgtgg cggagcagtt gagagcc                                27

<210> SEQ ID NO 169
<211> LENGTH: 27
<212> TYPE: DNA
<213> ORGANISM: Artificial Sequence
<220> FEATURE:
<223> OTHER INFORMATION: capture probe HLA-A23 ITASA23B

<400> SEQUENCE: 169
ccttcacttt ccctgtctcc tcgtccc                                27

<210> SEQ ID NO 170
<211> LENGTH: 27
<212> TYPE: DNA
<213> ORGANISM: Artificial Sequence
<220> FEATURE:
<223> OTHER INFORMATION: capture probe HLA-A24 ITSA24A

<400> SEQUENCE: 170
gcccatgtgg cggagcagca gagagcc                                27

<210> SEQ ID NO 171
<211> LENGTH: 27
<212> TYPE: DNA
<213> ORGANISM: Artificial Sequence
<220> FEATURE:

<223> OTHER INFORMATION: capture probe HLA-A24 ITASA24B

<400> SEQUENCE: 171
tagcggagcg cgatccgcag gttctct                27

<210> SEQ ID NO 172
<211> LENGTH: 27
<212> TYPE: DNA
<213> ORGANISM: Artificial Sequence
<220> FEATURE:
<223> OTHER INFORMATION: capture probe HLA-A25 ITASA25A

<400> SEQUENCE: 172
tagcggagcg cgatccgcag gctctct                27

<210> SEQ ID NO 173
<211> LENGTH: 27
<212> TYPE: DNA
<213> ORGANISM: Artificial Sequence
<220> FEATURE:
<223> OTHER INFORMATION: capture probe HLA-A25 ITASA25B

<400> SEQUENCE: 173
tcacattccg tgtgttccgg tcccaat                27

<210> SEQ ID NO 174
<211> LENGTH: 27
<212> TYPE: DNA
<213> ORGANISM: Artificial Sequence
<220> FEATURE:
<223> OTHER INFORMATION: capture probe HLA-A26 ITASA26

<400> SEQUENCE: 174
gggtccccag gttcgctcgg tcagtct                27

<210> SEQ ID NO 175
<211> LENGTH: 27
<212> TYPE: DNA
<213> ORGANISM: Artificial Sequence
<220> FEATURE:
<223> OTHER INFORMATION: capture probe HLA-A29 ITASA29

<400> SEQUENCE: 175
tcacattccg tgtctgcagg tcccaat                27

<210> SEQ ID NO 176
<211> LENGTH: 27
<212> TYPE: DNA
<213> ORGANISM: Artificial Sequence
<220> FEATURE:
<223> OTHER INFORMATION: capture probe HLA-A30 ITASA30

<400> SEQUENCE: 176
cgtaggcgtg ctgttcatac ccgcgga                27

<210> SEQ ID NO 177
<211> LENGTH: 27
<212> TYPE: DNA
<213> ORGANISM: Artificial Sequence
<220> FEATURE:
<223> OTHER INFORMATION: capture probe HLA-A31 ITASA31

<400> SEQUENCE: 177
cccaatactc aggcctctcc tgctcta                27

<210> SEQ ID NO 178
<211> LENGTH: 27
<212> TYPE: DNA
<213> ORGANISM: Artificial Sequence
<220> FEATURE:
<223> OTHER INFORMATION: capture probe HLA-A33 ITSA33

<400> SEQUENCE: 178
cgcacggacc cccccaggac gcatatg                                27

<210> SEQ ID NO 179
<211> LENGTH: 27
<212> TYPE: DNA
<213> ORGANISM: Artificial Sequence
<220> FEATURE:
<223> OTHER INFORMATION: capture probe HLA-A68 ITSA68A

<400> SEQUENCE: 179
ggcggcccat gtggcggagc agtggag                                27

<210> SEQ ID NO 180
<211> LENGTH: 27
<212> TYPE: DNA
<213> ORGANISM: Artificial Sequence
<220> FEATURE:
<223> OTHER INFORMATION: capture probe HLA-A68 ITASA68B

<400> SEQUENCE: 180
gtcgtaggcg tcctgccggt acccgcg                                27

<210> SEQ ID NO 181
<211> LENGTH: 27
<212> TYPE: DNA
<213> ORGANISM: Artificial Sequence
<220> FEATURE:
<223> OTHER INFORMATION: capture probe HLA-A69 ITASA69

<400> SEQUENCE: 181
atcctctgga cggtgtgaga accggcc                                27

<210> SEQ ID NO 182
<211> LENGTH: 15
<212> TYPE: DNA
<213> ORGANISM: Artificial Sequence
<220> FEATURE:
<223> OTHER INFORMATION: sense primer for cytochrome P450

<400> SEQUENCE: 182
gccagagcct gagga                                             15

<210> SEQ ID NO 183
<211> LENGTH: 20
<212> TYPE: DNA
<213> ORGANISM: Artificial Sequence
<220> FEATURE:
<223> OTHER INFORMATION: primer consensus a3, a23, a1, a2  antisense

<400> SEQUENCE: 183
tcaaaagaaa ttaacagaga                                        20

<210> SEQ ID NO 184
<211> LENGTH: 19
<212> TYPE: DNA
<213> ORGANISM: Artificial Sequence
<220> FEATURE:
<223> OTHER INFORMATION: primer Specific a9  antisense

```
<400> SEQUENCE: 184
acaatgaagg taacatagg                                              19

<210> SEQ ID NO 185
<211> LENGTH: 18
<212> TYPE: DNA
<213> ORGANISM: Artificial Sequence
<220> FEATURE:
<223> OTHER INFORMATION: primer Specific a18  antisense

<400> SEQUENCE: 185
actgatggaa ctaactgg                                               18

<210> SEQ ID NO 186
<211> LENGTH: 23
<212> TYPE: DNA
<213> ORGANISM: Artificial Sequence
<220> FEATURE:
<223> OTHER INFORMATION: capture probe 3a1

<400> SEQUENCE: 186
tgttttgatt cggtacatct ttg                                         23

<210> SEQ ID NO 187
<211> LENGTH: 21
<212> TYPE: DNA
<213> ORGANISM: Artificial Sequence
<220> FEATURE:
<223> OTHER INFORMATION: capture probe 3a3

<400> SEQUENCE: 187
ttgatttggt acatctttgc t                                           21

<210> SEQ ID NO 188
<211> LENGTH: 20
<212> TYPE: DNA
<213> ORGANISM: Artificial Sequence
<220> FEATURE:
<223> OTHER INFORMATION: capture probe 3A9

<400> SEQUENCE: 188
actcctgggg gttttgggtg                                             20

<210> SEQ ID NO 189
<211> LENGTH: 24
<212> TYPE: DNA
<213> ORGANISM: Artificial Sequence
<220> FEATURE:
<223> OTHER INFORMATION: capture probe 3A18

<400> SEQUENCE: 189
attactgagt attcagaaat tcac                                        24

<210> SEQ ID NO 190
<211> LENGTH: 25
<212> TYPE: DNA
<213> ORGANISM: Artificial Sequence
<220> FEATURE:
<223> OTHER INFORMATION: capture probe 3A2

<400> SEQUENCE: 190
ggttaaagat ttggtacatt tatgg                                       25

<210> SEQ ID NO 191
<211> LENGTH: 22
```

-continued

```
<212> TYPE: DNA
<213> ORGANISM: Artificial Sequence
<220> FEATURE:
<223> OTHER INFORMATION: consensus primer OGM1

<400> SEQUENCE: 191
cgtcttcaaa gcaagtggat tg                                              22

<210> SEQ ID NO 192
<211> LENGTH: 20
<212> TYPE: DNA
<213> ORGANISM: Artificial Sequence
<220> FEATURE:
<223> OTHER INFORMATION: consensus primer OGM2

<400> SEQUENCE: 192
atcctgttgc cggtcttgcg                                                 20
```